United States Patent
Gerbec et al.

(10) Patent No.: US 6,887,276 B2
(45) Date of Patent: May 3, 2005

(54) MODULAR IMPLANT FOR JOINT RECONSTRUCTION AND METHOD OF USE

(75) Inventors: Daniel E Gerbec, Logan, UT (US); T. Wade Fallin, Hyde Park, UT (US); Daniel F. Justin, Logan, UT (US)

(73) Assignee: Medicine Lodge, Inc, Logan, UT (US)

( * ) Notice: Subject to any disclaimer, the term of this patent is extended or adjusted under 35 U.S.C. 154(b) by 0 days.

(21) Appl. No.: 10/319,139

(22) Filed: Dec. 13, 2002

(65) Prior Publication Data

US 2004/0117024 A1 Jun. 17, 2004

(51) Int. Cl.$^7$ .................................................. A61F 2/30
(52) U.S. Cl. ................ 623/18.11; 623/19.12; 623/20.15; 623/20.34; 623/22.42
(58) Field of Search .................. 623/18.11, 19.11, 623/19.12, 19.13, 20.14, 20.15, 20.21, 20.22, 20.23, 20.24, 20.28, 20.34, 22.11, 22.15, 22.4, 22.41, 22.42, 22.43, 22.44, 22.45, 22.46, 23.15, 23.18, 23.23, 23.26, 23.32, 23.33, 23.35, 23.4, 23.44, 23.45, 23.46, 23.47

(56) References Cited

U.S. PATENT DOCUMENTS

| | | |
|---|---|---|
| 2,682,265 A | 6/1954 | Collison |
| 2,785,673 A | 3/1957 | Anderson |
| 3,806,957 A | 4/1974 | Shersher |
| 3,848,272 A | 11/1974 | Noiles |
| 3,875,593 A | 4/1975 | Shersher |
| 3,906,550 A | 9/1975 | Rostoker et al. |
| 3,943,576 A | 3/1976 | Sivash |
| 3,987,499 A | 10/1976 | Scharbach et al. |
| 4,016,651 A | 4/1977 | Kawahara et al. |
| 4,051,559 A | 10/1977 | Pifferi |
| 4,086,701 A | 5/1978 | Kawahara et al. |
| 4,259,072 A | 3/1981 | Hirabayashi et al. |

(Continued)

FOREIGN PATENT DOCUMENTS

| | | |
|---|---|---|
| DE | 32 05 577 A1 | 10/1982 |
| DE | 33 40 767 A1 | 5/1985 |
| DE | 40 31 520 A1 | 4/1992 |
| EP | 0 000 549 A1 | 2/1979 |
| EP | 0 201 407 A1 | 11/1986 |
| EP | 0 283 706 A1 | 9/1988 |
| EP | 00336774 A1 | 10/1989 |
| EP | 0 359 457 A1 | 3/1990 |
| EP | 00376658 A2 | 7/1990 |
| EP | 0 433 121 A1 | 6/1991 |
| EP | 00495340 A1 | 7/1992 |
| EP | 00336774 B1 | 12/1992 |
| EP | 00556997 A1 | 8/1993 |
| EP | 00714645 A1 | 6/1996 |
| EP | 00832620 A3 | 1/1999 |
| EP | 00878177 A3 | 2/1999 |
| EP | 00913132 A1 | 5/1999 |
| EP | 00714645 B1 | 5/2000 |
| WO | WO03086244 A1 | 10/2003 |
| WO | WO03094803 A1 | 11/2003 |
| WO | WO04028413 A1 | 4/2004 |

(Continued)

*Primary Examiner*—Corrine McDermott
*Assistant Examiner*—Thomas J Sweet
(74) *Attorney, Agent, or Firm*—David W. Meibos; Daniel F. Justin

(57) ABSTRACT

Modular orthopedic implants for joint reconstruction and methods of use therein are described that comprise base, body, and stem components. The base receives an articulating portion on a first end and has a connector on a second end that mates with the body and stem. The tubular body has a tissue engaging external portion, and an internal bore. The stem has an elongated shaft configured to be situated inside of a bone, and a top end having a connector. In a group of two-connection embodiments, the base mates with the body to form a first connection and the base mates with the stem to form a second connection. In a group of three connection embodiments, the stem and body also mate to form a third connection. The connections are combinations of interference fit connections such as press fits, multiple press fit and tapered fit connections.

66 Claims, 24 Drawing Sheets

U.S. PATENT DOCUMENTS

| | | | |
|---|---|---|---|
| 4,304,011 A | 12/1981 | Whelam, III | |
| 4,404,691 A | 9/1983 | Buning et al. | |
| 4,520,511 A | 6/1985 | Gianezio et al. | |
| 4,578,081 A | 3/1986 | Harder et al. | |
| 4,619,659 A | 10/1986 | Witzel | |
| 4,624,673 A | 11/1986 | Meyer | |
| 4,676,797 A | 6/1987 | Anapliotis et al. | |
| 4,714,471 A | 12/1987 | Grundei | |
| 4,790,854 A | 12/1988 | Harder et al. | |
| 4,822,366 A | 4/1989 | Bolesky | |
| 4,842,606 A | 6/1989 | Kranz et al. | |
| 4,846,839 A | 7/1989 | Noiles | |
| 4,851,007 A | 7/1989 | Gray | |
| 4,878,917 A | 11/1989 | Kranz et al. | |
| 4,908,032 A | 3/1990 | Keller | |
| 4,917,530 A | 4/1990 | Engelhardt et al. | |
| 4,919,678 A | 4/1990 | Kranz | |
| 4,936,853 A | 6/1990 | Fabian | |
| 4,938,773 A | 7/1990 | Strand | |
| 4,985,037 A | 1/1991 | Petersen | |
| 4,995,883 A | 2/1991 | Demane et al. | |
| 5,002,578 A | 3/1991 | Luman | |
| 5,002,581 A | 3/1991 | Paxson et al. | |
| 5,019,108 A | 5/1991 | Bertin et al. | |
| 5,026,280 A | 6/1991 | Dürr et al. | |
| 5,035,712 A | 7/1991 | Hoffman | |
| 5,058,936 A | 10/1991 | Kapgan et al. | |
| 5,080,676 A | 1/1992 | May | |
| 5,080,685 A | 1/1992 | Bolesky et al. | |
| 5,108,437 A | 4/1992 | Kenna | |
| 5,108,452 A | 4/1992 | Fallin | |
| 5,133,760 A | 7/1992 | Petersen et al. | |
| 5,133,771 A | 7/1992 | Duncan et al. | |
| 5,152,796 A | 10/1992 | Slamin | |
| 5,181,928 A | 1/1993 | Bolesky et al. | |
| 5,190,546 A | 3/1993 | Jervis | |
| 5,194,066 A | 3/1993 | Van Zile | |
| 5,197,720 A | 3/1993 | Renz et al. | |
| 5,201,882 A | 4/1993 | Paxson | |
| 5,286,260 A | 2/1994 | Bolesky et al. | |
| 5,314,479 A | 5/1994 | Rockwood, Jr. et al. | |
| 5,342,366 A | 8/1994 | Whiteside et al. | |
| 5,344,457 A | 9/1994 | Pilliar et al. | |
| 5,370,706 A | 12/1994 | Bolesky et al. | |
| 5,489,309 A | 2/1996 | Lackey et al. | |
| 5,489,311 A | 2/1996 | Cipolletti | |
| 5,507,817 A | 4/1996 | Craig et al. | |
| 5,507,826 A | 4/1996 | Besselink et al. | |
| 5,507,830 A | 4/1996 | DeMane et al. | |
| 5,549,706 A | 8/1996 | McCarthy | |
| 5,580,247 A | 12/1996 | Gittleman | |
| 5,584,695 A | 12/1996 | Lal Sachdeva et al. | |
| 5,597,378 A | 1/1997 | Jervis | |
| 5,607,431 A | 3/1997 | Dudasik et al. | |
| 5,609,645 A | 3/1997 | Vinciguerra | |
| 5,645,607 A | 7/1997 | Hickey | |
| 5,653,764 A | 8/1997 | Murphy | |
| 5,653,765 A | 8/1997 | McTighe et al. | |
| 5,658,349 A | 8/1997 | Brooks et al. | |
| 5,665,121 A | 9/1997 | Gie et al. | |
| 5,683,404 A | 11/1997 | Johnson | |
| 5,702,480 A | 12/1997 | Kroph et al. | |
| 5,702,486 A | 12/1997 | Craig et al. | |
| 5,725,592 A | 3/1998 | White et al. | |
| 5,755,720 A | 5/1998 | Mikhail | |
| 5,766,262 A | 6/1998 | Mikhail | |
| 5,766,263 A | 6/1998 | Grundei et al. | |
| 5,776,200 A | 7/1998 | Johnson et al. | |
| 5,782,921 A | 7/1998 | Colleran et al. | |
| 5,791,899 A | 8/1998 | Sachdeva et al. | |
| 5,858,020 A | 1/1999 | Johnson et al. | |
| 5,860,982 A | 1/1999 | Ro et al. | |
| 5,876,459 A | 3/1999 | Powell | |
| 5,885,295 A | 3/1999 | McDaniel et al. | |
| 5,888,206 A | 3/1999 | Lob et al. | |
| 5,888,208 A | 3/1999 | Ro | |
| 5,902,340 A | 5/1999 | White et al. | |
| 5,906,644 A | 5/1999 | Powell | |
| 5,931,871 A | 8/1999 | Baur et al. | |
| 5,944,756 A | 8/1999 | Fischetti et al. | |
| 5,954,725 A | 9/1999 | Sherman et al. | |
| 5,976,147 A | 11/1999 | LaSalle et al. | |
| 5,976,188 A | 11/1999 | Dextradeur et al. | |
| 6,048,365 A | 4/2000 | Burrows et al. | |
| 6,074,424 A | 6/2000 | Perrone, Jr. et al. | |
| 6,086,614 A | 7/2000 | Mumme | |
| 6,090,146 A | 7/2000 | Rozow, III et al. | |
| 6,102,956 A | 8/2000 | Kranz | |
| 6,109,602 A | 8/2000 | Schron, Jr. et al. | |
| 6,126,691 A | 10/2000 | Kasra et al. | |
| 6,136,035 A | 10/2000 | Lob et al. | |
| 6,139,584 A | 10/2000 | Ochoa et al. | |
| 6,165,223 A | 12/2000 | Metzger et al. | |
| 6,193,759 B1 | 2/2001 | Ro et al. | |
| 6,197,063 B1 | 3/2001 | Dews | |
| 6,203,575 B1 | 3/2001 | Farey | |
| 6,210,413 B1 | 4/2001 | Justis et al. | |
| 6,214,052 B1 | 4/2001 | Burkinshaw | |
| 6,214,053 B1 | 4/2001 | Ling et al. | |
| 6,257,593 B1 | 7/2001 | White | |
| 6,264,699 B1 | 7/2001 | Noiles et al. | |
| 6,273,915 B1 | 8/2001 | Grimes | |
| 6,290,726 B1 | 9/2001 | Pope et al. | |
| 6,299,648 B1 | 10/2001 | Doubler et al. | |
| 6,306,174 B1 | 10/2001 | Gie et al. | |
| 6,319,286 B1 | 11/2001 | Fernandez et al. | |
| 6,379,388 B1 | 4/2002 | Ensign et al. | |
| 6,702,854 B1 | 3/2004 | Cheal et al. | |
| 2002/0004685 A1 | 1/2002 | White | |
| 2002/0007220 A1 | 1/2002 | Gie et al. | |
| 2002/0072799 A1 * | 6/2002 | Despres et al. | 623/16.11 |
| 2002/0072802 A1 | 6/2002 | O'Neil | |
| 2002/0103541 A1 | 8/2002 | Meyers | |
| 2003/0074078 A1 * | 4/2003 | Doubler et al. | 623/22.42 |
| 2003/0074079 A1 | 4/2003 | McTighe et al. | |
| 2003/0171819 A1 | 9/2003 | Sotereanos | |
| 2004/0054419 A1 | 3/2004 | Serra et al. | |

FOREIGN PATENT DOCUMENTS

| | | |
|---|---|---|
| EP | 01004283 A2 | 5/2000 |
| EP | 01132064 A2 | 9/2001 |
| EP | 1344505 A2 | 9/2003 |
| FR | 2 225 141 | 11/1974 |
| FR | 2 705 558 | 12/1994 |
| WO | WO 83/02555 | 8/1983 |
| WO | WO 85/03426 | 8/1985 |
| WO | WO 86/02260 | 4/1986 |
| WO | WO 86/06954 | 12/1986 |
| WO | WO 91/17723 | 11/1991 |
| WO | WO09118563 A1 | 12/1991 |
| WO | WO09613233 A1 | 5/1996 |
| WO | WO09720525 A1 | 6/1997 |
| WO | WO09808467 A1 | 3/1998 |
| WO | WO09808468 A1 | 3/1998 |
| WO | WO 99/47081 | 9/1999 |
| WO | WO 00/72784 A1 | 12/2000 |
| WO | WO0167997 A1 | 9/2001 |
| WO | WO00207647 A2 | 1/2002 |
| WO | WO03028594 A1 | 4/2003 |

* cited by examiner

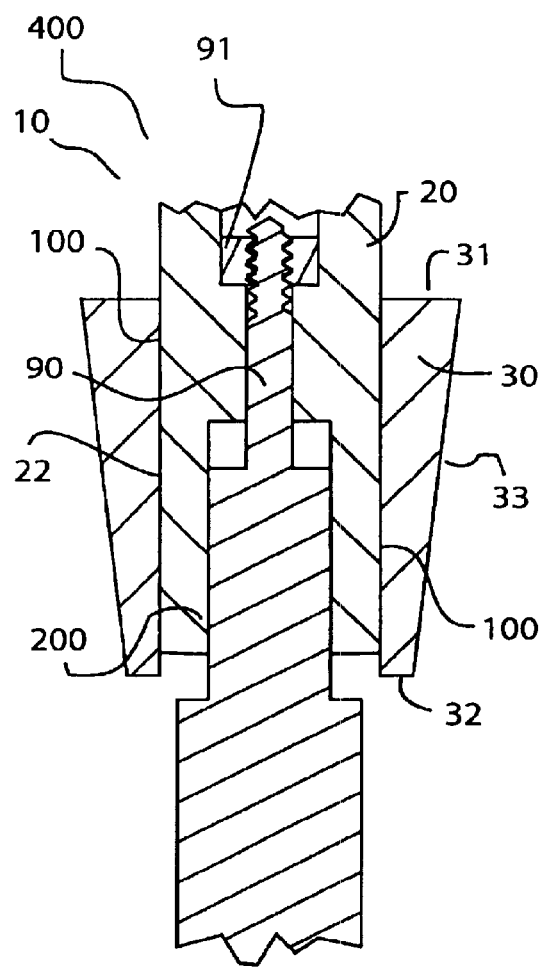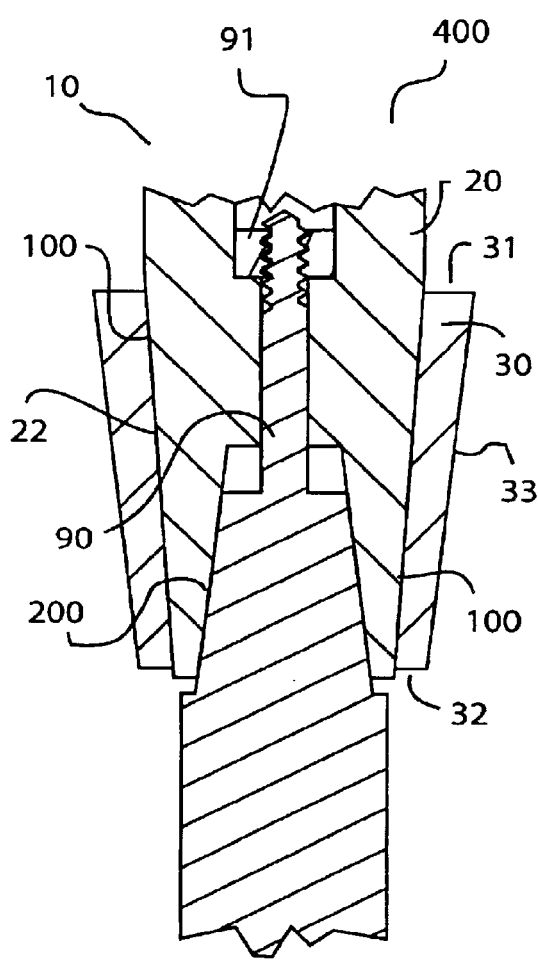
Fig. 22A                    Fig. 22B

MODULAR IMPLANT FOR JOINT RECONSTRUCTION AND METHOD OF USE

CROSS-REFERENCE TO RELATED APPLICATIONS

Not applicable.

BACKGROUND OF THE INVENTION

1. The Field of the Invention

The present invention relates to a modular prosthesis for replacing a portion of a bone and the methods of assembly and use thereof.

2. The Relevant Technology

As the average age of society increases and the expected quality of medical treatment increases, the occurrence of surgical procedures to repair or replace worn arthritic joints correspondingly increases. Consequently, the surgical replacement of articulating joints is becoming more common. In the replacement of an articulating joint, one end of the prosthesis is placed within a bone on one side of a joint. Placing the prosthesis within the bone allows adequate mechanical stabilization between the bone and the implant. The opposite side of the prosthesis is configured to functionally replace the removed articulating end of the bone and provide a joint articulation surface.

The bone is prepared for the prosthesis by first resecting the bone and removing the damaged articulating end of the bone. This exposes the inside of the bone. Then, in the case of long bones, tools such as reamers, broaches and other bone tissue removal instruments are used to create a bone cavity that extends from the resection down into the intramedullary canal. Oftentimes bone cement is then added to the cavity, creating a bone cement mantle between the prosthesis and the bone. Sometimes the shape cavity is prepared to closely match external surface of the prosthesis, and no bone cement is used.

Once the bone cavity is prepared, the prosthesis is placed into the bone cavity and is supported by the internal bone tissue or bone cement mantle. Then, the prosthesis is positioned such that the articulating end of the implant articulates with the opposite side of the natural joint in the case of a hemiplasty, or articulates with a corresponding implant replacing the opposite side of the joint in the case of an arthroplasty.

A successful joint replacement procedure restores the biomechanical function of the joint while maintaining a secure interface with the bone, allowing the loads on the joint to be distributed optimally. A closely matching fit between the prosthesis and the bone issue helps to stabilize the prosthesis and transfer the loads from the implant to the bone efficiently. Operating room centers need to keep in inventory an extraordinary number of single piece prostheses to provide single piece prostheses that optimally fit each size and shape of patient requiring a joint replacement surgery. With single piece prostheses, one compromise is to stock fewer prostheses shapes and sizes. However, this results in some patients receiving prostheses that are not ideally suited for their bone anatomy.

Modular components of joint reconstruction implants have been developed as an alternative to single piece joint reconstruction prostheses to help reduce inventory and optimize fit. The functional portions of single piece joint prostheses are sectioned into modular components. Each of these components is available in a variety of shapes and a range of sizes. Shapes and sizes of each component in the range that best fits a given patent's anatomy are supplied to the surgeon at the time of surgery. The surgeon selects the optimal combination of components to build the best fitting prosthesis. These modular components are then mated together and secured by locking the mechanical connections between them.

A successful modular implant system is one that provides the surgeon with a wide range of anatomical shapes and sizes, limits the inventory needed on hand, and provides reliable mating connections between the components. Successful application of the modular implants depends on careful selection, insertion, positioning and assembly of the components to best fit the existing bone and to restore the natural anatomy. To achieve this, it is important that the modular implant design allow for a functional and practical assembly process that results in strong mechanical bonds between the components.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 22A is a close-up cross-sectional view of a two-connection embodiment of the modular implant showing a press fit connection between the base and the body, a press fit connection between the base and the stem, and a securing element protrusion protruding from the stem and passing through the body and through the base to the first end of the base, with threads received by a securing fastener;

FIG. 22B is a close-up cross-sectional view of a two-connection embodiment of the modular implant showing a tapered connection between the base and the body, a tapered connection between the base and the stem, and a securing element protrusion protruding from the stem and passing through the body and through the base to the first end of the base, with threads received by a securing fastener;

DETAILED DESCRIPTION OF THE PREFERRED EMBODIMENTS

Figure 1:
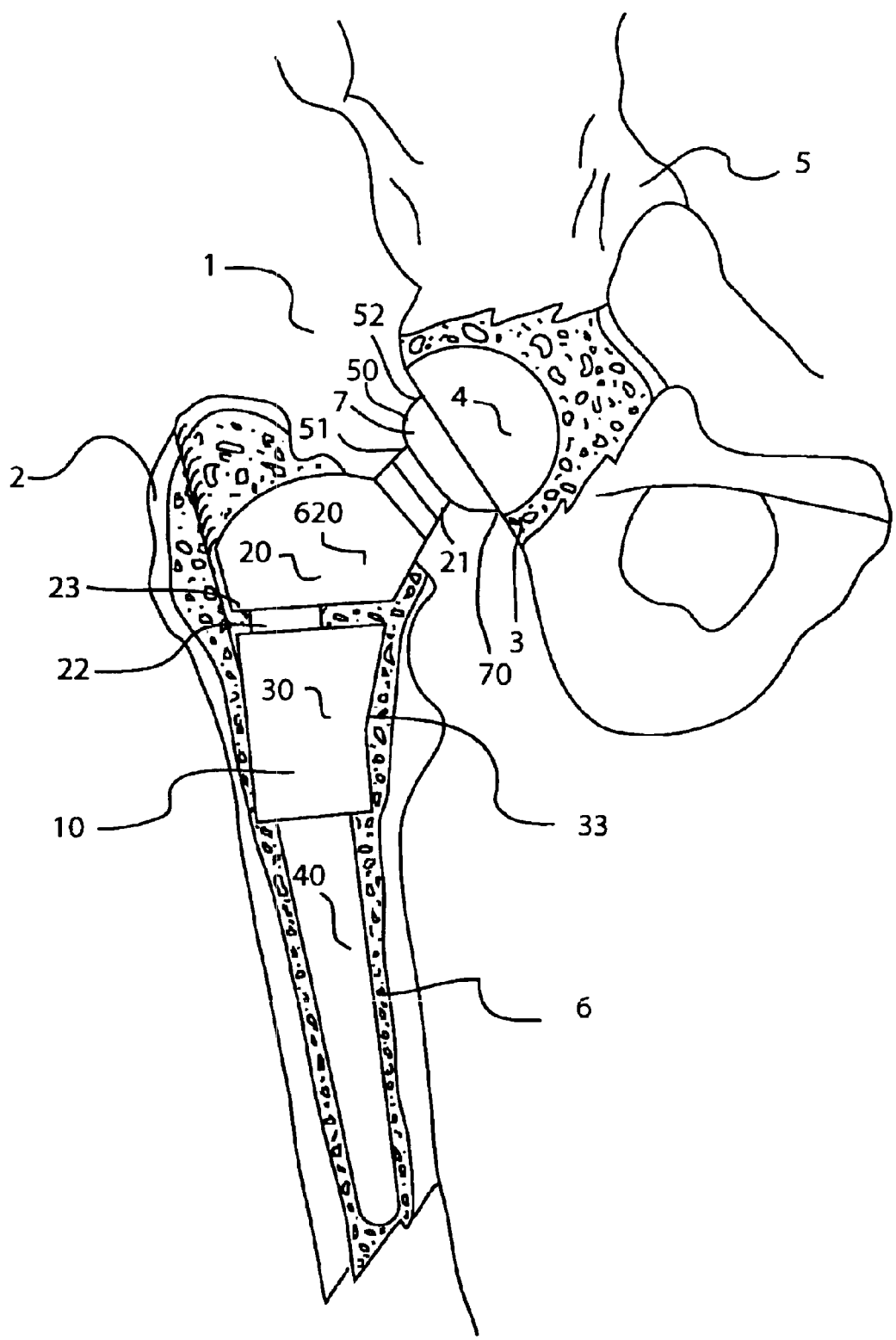
FIG. 1 is an anterior cross-sectional view of a modular implant for arthroplasty of a hip joint showing the modular implant in the femur and an artificial acetabular implant in the pelvis.

Referring to FIG. 1, a modular implant 10 for joint replacement is shown implanted in a proximal femur 2 of a human hip joint 1. This anterior cross-sectional view shows a result of an arthroplasty procedure in the hip joint 1 in which the modular implant 10 is in the proximal femur 2 and an acetabular implant 4 replaces the bearing cartilage in an acetabulum or hip socket 3 of a pelvis 5. A femoral head component 7 is a metal or ceramic ball that articulates in the acetabulum 3. The femoral head component 7 replaces the resected and removed natural proximal spherical femoral head (not shown) and the associated articular cartilage. The modular implant 10 adapted for the proximal femur 2 in the hip joint 1 is typically a metal prosthesis implanted in a femoral intramedullary canal 6 of the proximal femur 2. It connects the proximal femur 2 bone to the femoral head component 7 and distributes the major hip loads from the acetabular socket 3 to the femoral intramedullary canal 6.

The modular implant 10 comprises a base 20, a body 30 and a stem 40. The base 20 has a first end 21 and an interference fit connector 22 on a second end 23. The modular implant 10 articulates either with another prosthetic articulating component in the joint as in the case of an hip arthroplasty as shown in FIG. 1, or with the joint tissue directly as shown in the case of a shoulder hemiplasty in FIG. 4. In the case of an arthroplasty, the first end 21 of the base 20 can be shaped to articulate directly with an articulating portion 70 of an opposing joint implant surface, or configured to receive a bottom end 51 of an articulating surface component 50 that articulates with the articulating portion 70 of an opposing joint implant surface. In the case of a hemiplasty, the first end 21 of the base 20 can be shaped to articulate directly with an anatomic joint surface or configured to receive the bottom end 51 of the articulating surface component 50 that is shaped to articulate with an anatomic joint surface.

In FIG. 1, the articulating surface component 50 is attached to the base 20. The articulating surface component 50 has the bottom end 51 and an articulating end 52. In this example, the articulating surface component 50 is shaped to receive the first end 21 of the base 20 on the bottom end 51 and receive the acetabular implant 4 on the articulating end 52. In this case in which the modular implant 10 is configured for the proximal femur 2 in the hip joint 1, the articulating surface component 50 is the femoral head component 7 and is shaped similarly to the ball of the resected natural anatomic femoral head (not shown).

In the case of this femoral modular implant 10 for hip joint replacement, the modular implant 10 is configured to fit inside of the proximal femur 2. The shape and size of the base 20, body 30 and stem 40 components are chosen to best fit the inside of the proximal femur 2. Configurations of the modular implant 10 for other bones of other joints will be described in reference to forthcoming descriptions.

Figure 2:
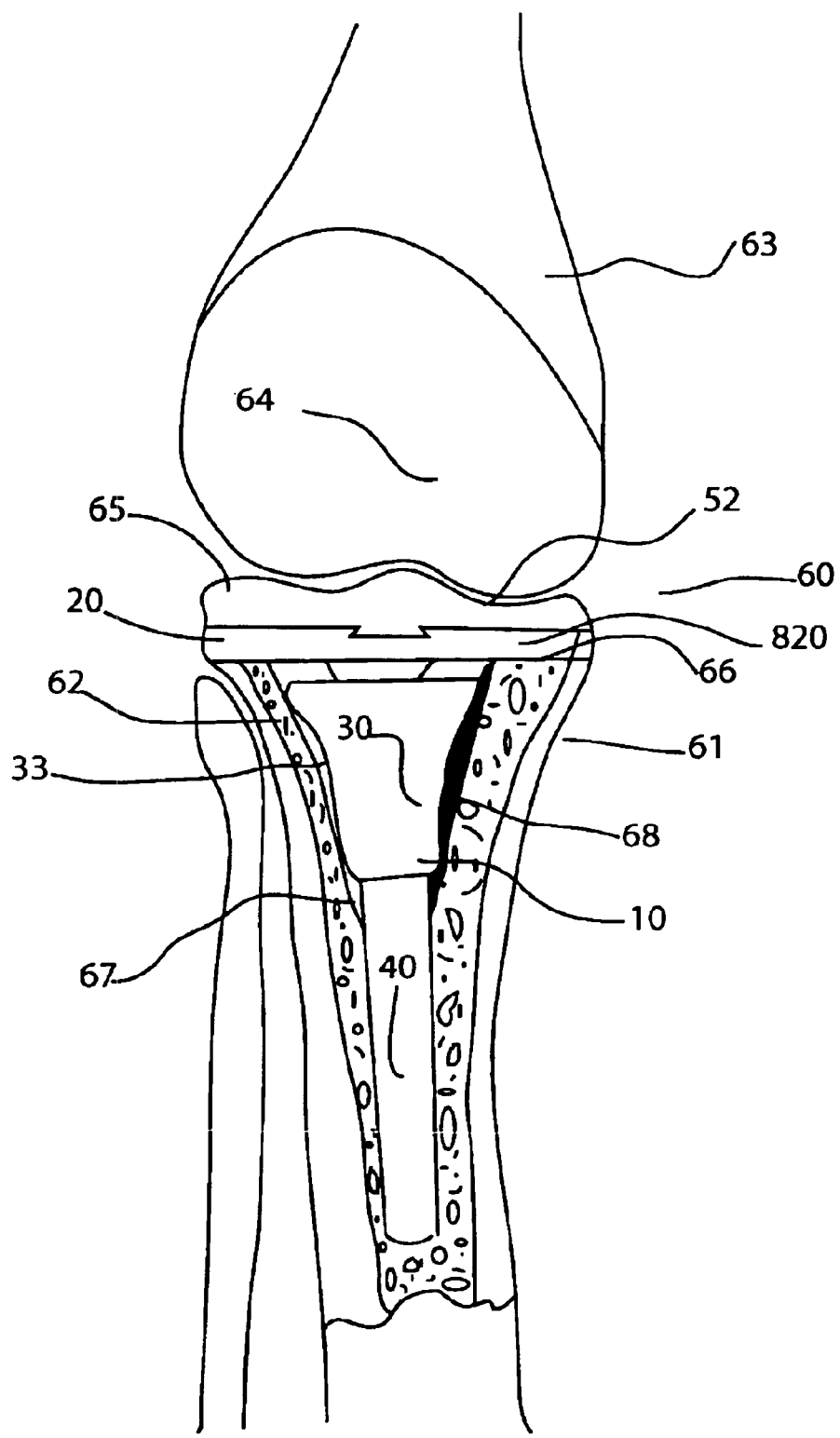
FIG. 2 is an anterior cross-sectional view of a modular implant for arthroplasty of a knee joint showing the modular implant in the proximal tibia and an artificial femoral implant attached to the distal femur.

FIG. 2 shows an anterior cross-sectional view of the modular implant 10 for arthroplasty of a knee joint 60 showing the modular implant 10 in a proximal tibia 61 and a distal femoral implant 64 attached to a distal femur 63. In this example, the base 20 is adapted to receive a knee tibial articulating surface component 65 that is shaped to represent the anatomic geometry of the removed human proximal tibia articulating surface (not shown) and articulate with either the distal femoral articular cartilage (not shown) or the distal femoral knee implant 64. The base 20 is shaped to cover a proximal tibial surface 66 exposed by the bone resection and mate with the body 30 and the stem 40. A tissue engaging portion 33 of the body 30 is shaped to fit into an inside 62 of the proximal tibia 61. In some cases the bone tissue on the inside 62 of the proximal tibia 61 is removed by a tissue removal process such that the tissue engaging portion 33 is snugly fit into a bone cavity 67. This allows bone to contact around the body 30 and structurally support the modular implant 10. In other cases, bone cement is placed into the prepared bone cavity 67 allowing a partial bone cement mantel 68 to form between the modular implant 10 and the bone cavity 67 such that the modular implant 10 is structurally supported by a combination of the partial bone cement mantel 68 and the bone cavity 67.

Figure 3:
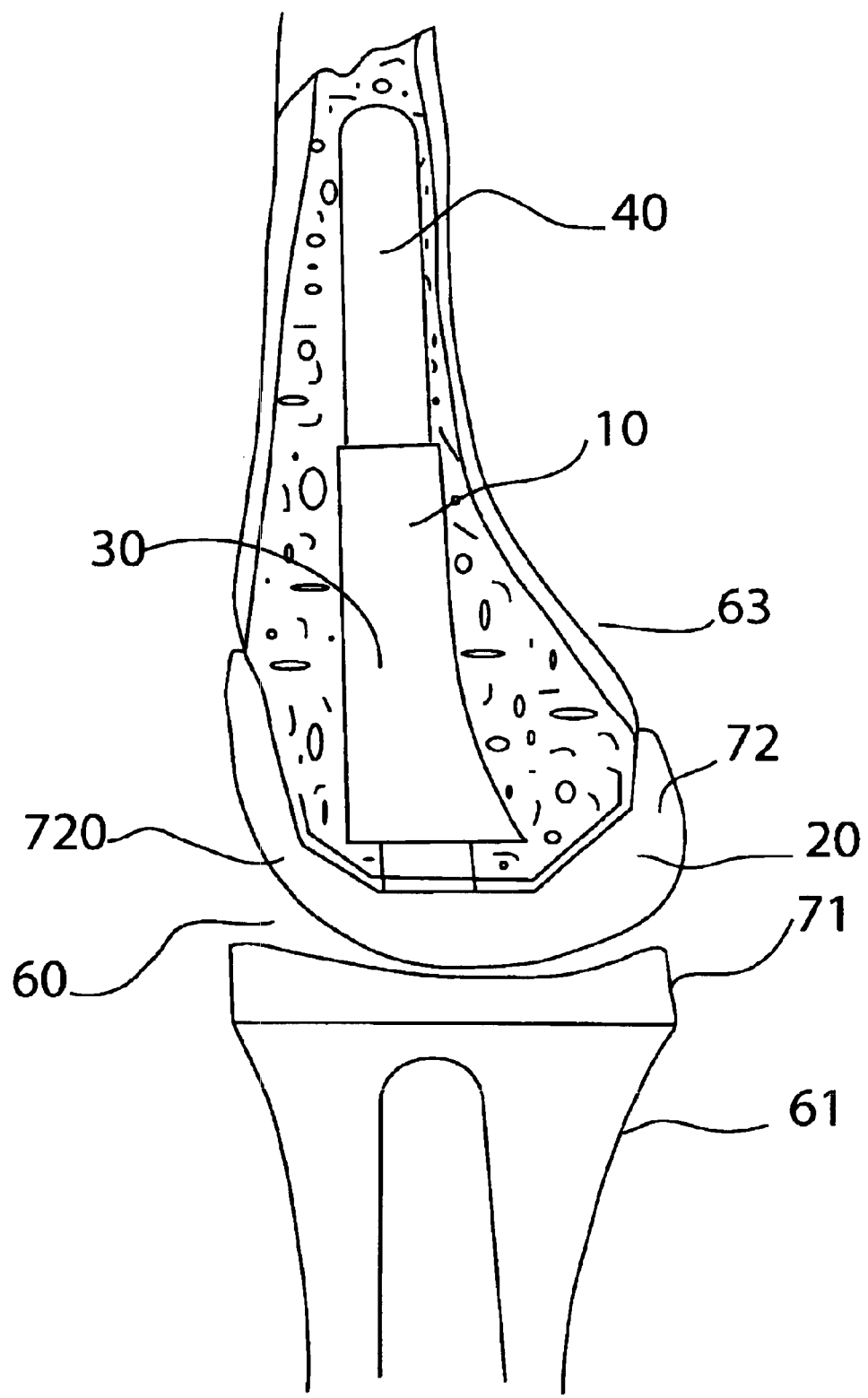
FIG. 3 is a lateral cross-sectional view of a modular implant for arthroplasty of a knee joint showing the modular implant replacing the articular tissue of the distal femur and an artificial tibial implant attached to the proximal tibia.

A lateral cross-sectional view of the modular implant 10 for arthroplasty of a knee joint 60 is shown in FIG. 3. The modular implant 10 is replacing the articular tissue (not shown) of the distal femur 63. A tibial implant 71 is shown attached to the proximal tibia 61. In this case an articulating portion 72 of the modular implant 10 is shaped similarly to the removed distal femoral condyles (not shown).

Figure 4:
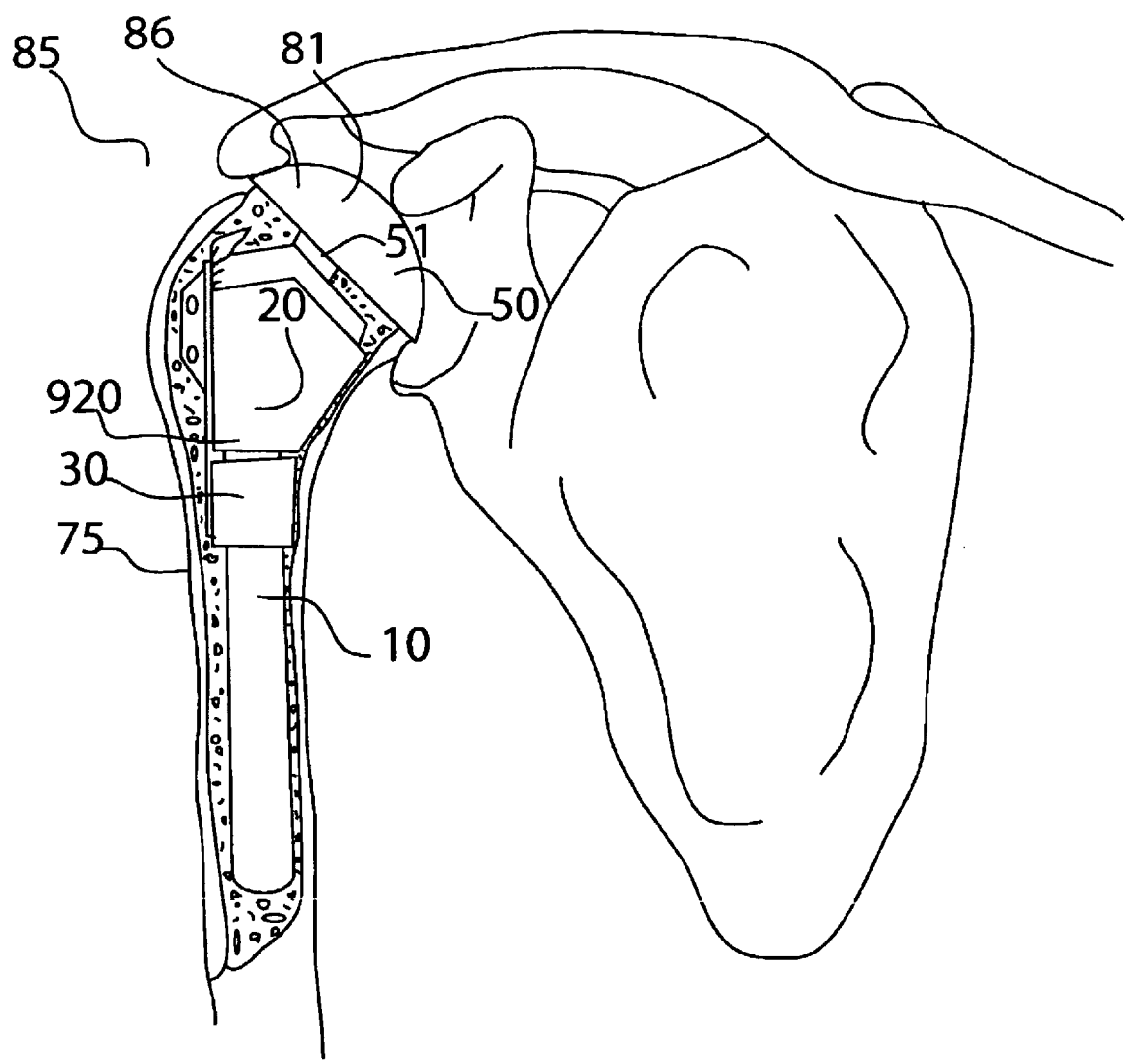
FIG. 4 is an anterior cross-sectional view of a modular implant for hemiplasty joint reconstruction in a shoulder joint showing the modular implant in the humerus articulating against the natural articulating tissue of the acromium.

An anterior cross-sectional view of the modular implant 10 for hemiplasty joint reconstruction in a shoulder joint 85 is shown in FIG. 4. In this example, the modular implant 10 in a humerus 75 is articulating against an articulating cartilage surface 86 of the acromium 81.

Modular implants for joint reconstruction are applicable in the hip, knee, ankle, foot, shoulder, elbow, wrist, hand, spine, and any other human joint in which articulating cartilage is being replaced by a prosthesis. However, only the hip, knee, and shoulder implants are described in detail by way of example in this detailed description. Methods of use and techniques referred to herein are also applicable to the hip, knee, ankle, foot, shoulder, elbow, wrist, hand, spine, and any other human joint in which articulating cartilage is being replaced by a prosthesis.

Figure 5:
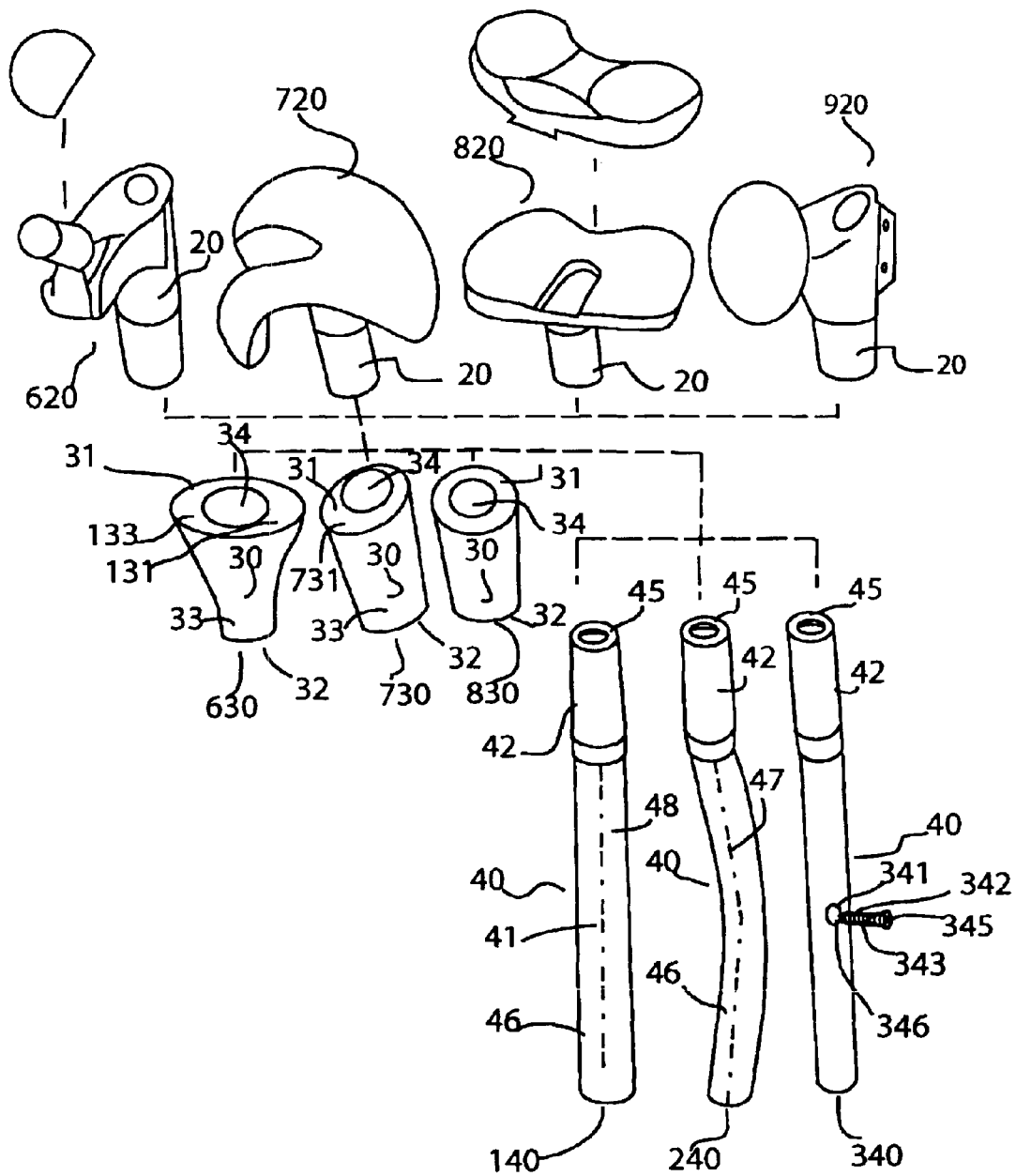
FIG. 5 is an exploded view schematically demonstrating possible interconnections between various modular components including base components optimally shaped for best use as a proximal femoral hip component, a proximal tibial knee component, a distal femur knee component, and a proximal humerus shoulder component, various shapes of body components, and various shapes of stem components.

FIG. 5 is an exploded view schematically demonstrating possible interconnections between various modular components. Since modular implants 10 typically comprise a base 20, a body 30 and a stem 40, representative sets of various configurations of each the base 20, body 30, and stem 40 components are shown. Four examples of base 20 components are shown which are configured to match the specific joint replacement application. A proximal femoral hip base component 620, a distal femoral knee base component 720, a proximal tibial knee base component 820, and a proximal humerus shoulder base component 920 are shown in FIG. 5.

Three tubular body 30 configurations are also shown in FIG. 5. Each of the three configurations shown has a top end 31, a bottom end 32, the tissue engaging portion 33 between the top end 31 and the bottom end 32. Each also has an internal bore 34 passing through the top end 31 and through the bottom end 32. The first configuration 630 of the body 30 has a tissue engaging portion 33 with two lateral protrusions 131 extending the tissue engaging portion 33 of the body 30 on opposite sides, near the top end 31. Although not limited to use as a body 20 for use with the tibial base 820, the first configuration 630 is suitable for use in the proximal tibia 61 in knee joint 60 modular implant 10 applications. A second configuration 730 of the body 30 has the tissue engaging portion 33 with a single lateral protrusion 731 extending the tissue engaging portion 33 near the top end 31 of the body in one direction. Although not limited to use as a body 20 for use with the proximal femoral base hip component 620, the second configuration 730 of the base 30 is suitable for use in the proximal femur 2 in hip joint 1 modular implant 10 applications. A third configuration 830 has a tissue engaging portion 33 that is circumferentially larger at the top end 31 than at the bottom end 32.

Three configurations of the stem 40 are shown schematically in FIG. 5. These three are shown to demonstrate some of the possible stem configurations applicable to the stem 40. It is understood that other stem configurations (not shown), that are necessary to match a specific patient population's anatomy, and combinations of the stem configurations described can be applied to the modular implant 10 and can be incorporated into the methods and techniques described herein for the use of the stem 40. The three configurations of the stem 40 shown have a bottom end 46 and an elongated shaft 41 adjacent to the bottom end 46. The elongated shaft 41 is configured to be situated inside of bone. Adjacent to the elongated shaft 41, the stem has a top end 42 having an interference fit connector 45. In some cases, a straight stem 48 is preferred such as shown in a first configuration 140. In other cases, due to anatomic considerations such as a bone, a bow 47 to the stem 40 is preferred such as shown in a second stem configuration 240. In still other cases, a bone locking feature 49 is preferred on the stem 40 such as shown in a third configuration 340. In the third configuration 340, a bore 341 through the elongated shaft 41 of the stem 40 is positioned to mate with a corresponding fastener 342. The fastener 342 has a central shaft 343 with an adjacent head 345. Attached to the side opposite the head 345 on the central shaft 343 is a mating feature 346 that is configured to pass through the bone tissue and into the bore 341 in the elongated shaft 41 of the stem 40. The shaft 343 is also configured to pass through the bone tissue and into the bore 341. When the fastener 342 is in the bone and locked through the bore 341 it augments the fixation of the stem 40 in the bone.

Configurations of the mechanical connecting features between the base 20, body 30, and stem 40 are shown in FIGS. 6–24. The modular implants 10 shown in FIGS. 6–9, FIG. 18, FIG. 20, FIG. 22 are examples of a two-connection embodiment 400 in which a first connection 100 joins the base 20 and the body 30, and a second connection 200 joins the base 20 and the stem 40. Thus, the two-connection embodiments 400 of the modular implant 10 provide two connection regions.

The modular implants 10 shown in FIGS. 10–17, FIG. 19, FIG. 21, and FIGS. 23–24 are examples of a three-connection embodiment 500 in which the first connection 100 joins the base 20 and the body 30, the second connection 200 joins the base 20 and the stem 40, and a third connection 300 joins the body 20 and the stem 40. Thus, the three-connection embodiments 500 of the modular implant 10 provide three connection regions.

One type of a connection between two components is an interference fit connection. An interference fit occurs when the inner bore of an outside (female) piece is slightly less in size than the outer periphery of the inside (male) piece that is positioned inside of the internal bore of the female piece. When the two parts are mated together, the material on the inner bore and the material on the outer periphery interfere with each other, and the parts lock together. For the interference fit connection to be reliable, there must be sufficient interference between the inner bore and the outer periphery to maintain long-term integrity of the interference fit, but not so much interference to cause damage to the material of the assembly.

Various methods are used to position the pieces together in an interference fit connection. In the case of a press fit interference fit connection the two pieces are simply forced together by longitudinally pressing the outer periphery of the inside piece into the inner bore of the outside piece. In the case of a tapered fit interference fit connection the inside bore of the outer piece and the outer periphery of the inside piece have successively smaller diameters in the longitudinal direction. The two pieces are loosely placed together longitudinally until the inside bore and outside periphery surfaces meet. Then the two pieces are forced together by longitudinally pressing the outer periphery of the inside piece into the inner bore of the outside piece.

In the case of a shrink fit interference fit connection, the two pieces are loosely placed together longitudinally and a force differential is applied to the outside piece causing it to shrink around the inside piece. In the case of an expansion fit interference fit connection, the two pieces are loosely placed together longitudinally and a force differential is applied to the inside piece causing it to expand into the internal bore of the outside piece. In the case of a cam lock interference fit connection, the two pieces are loosely placed together longitudinally and a torque differential is applied between them causing them to lock together.

The two types of interference fit connections shown in FIGS. 6–23 are press fit connections and tapered fit connection. A press fit connection is a type of interference fit connection in which the outside piece and the inside piece are mated by pressing them together longitudinally. The inner bore of an outside piece is slightly less in size than the outer periphery of the piece inserted into the internal bore. Taper regions are generally configured with contiguous linearly increasing slope of about three degrees per side. This taper configuration is commonly referred to as a Morse type self locking taper and is used to connect orthopedic implant components such as modular intramedullary nails, modular femoral heads for hip joints and various modular knee implant components. However other configurations of taper angles with linear and non-linear, contiguous and non-contiguous slopes may be used.

Additionally, the length, position and configuration of the interference are critical to the correct function of the assembly. In some instances, such as in a connection that covers a long length or cases in which manufacturing dimensional tolerances of diameters must be held over long distances, it is preferable to section the interference fit into multiple zones of contact. These zones may be located near opposite ends of the interference fit region. The multiple zone interference fit connections shown in the figures are two zone press fit connections. However, any type of interference fit and any multiple of zones can be applied.

The connection described herein function independently of other connections in the respective assemblies. In the two-connection embodiment 400, the first connection 100 and the second connection 200 are mated and released independently of each other., In the three connection embodiment 500, the first connection 100, the second connection 200, and the third connection 300 are mated and released independently of each of the other connections.

Mated connections are connections between two components that are joined together and restrained by at least one mode of restrainment. These modes include tension, compression, bending, shear, torsion and combinations therein of these modes.

Interference fit connections are described herein as the preferred embodiment of connection between the base 20, body 30 and stem 40. However, other embodiments of connections known in the mechanical arts can also be applied between any two or any three of the base 20, body 30 and stem 40 components. These other embodiments of connections include expanding collet connections, epoxy connections, cemented connections, welded connections, threaded connections, brazed connections, sodered connections, or any connection requiring an interpositional element or elements that plastically or elastically deform to case the connection to mate or release.

Figure 6:
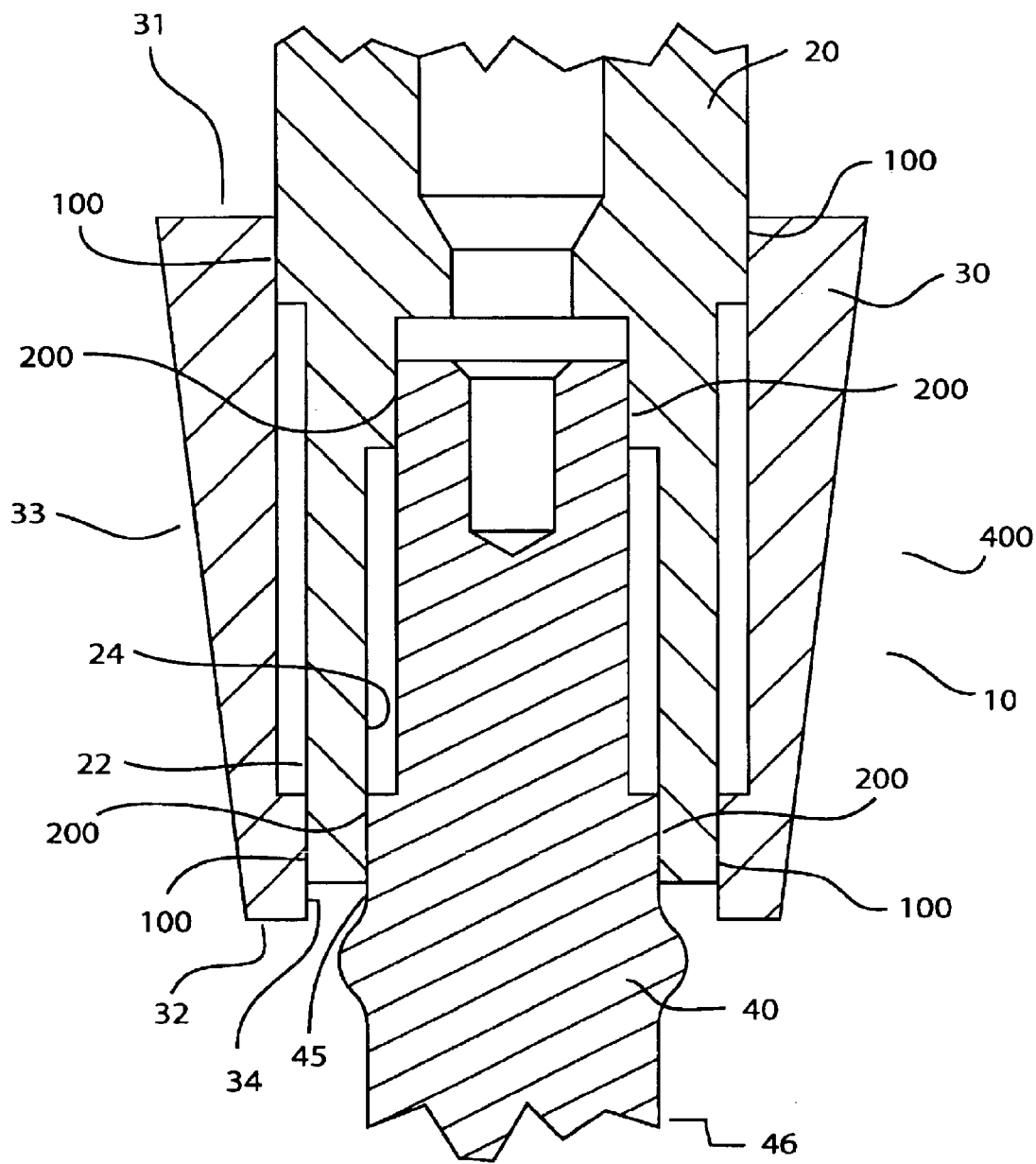
FIG. 6 is a close-up cross-sectional view of the connections between the components of a two-connection embodiment of the modular implant showing an interference fit connection between the base and the body and an interference fit connection between the base and the stem, where both of the interference fit connections are multiple zone press fit connections.

A two-connection embodiment 400 of the modular implant 10 is shown in FIG. 6 with the first connection 100 between the base 20 and the body 30, and the second connection 200 between the base 20 and the stem 40. The first connection 100 and the second connection 200 are both multiple zone press fit connections.

Although press fit and tapered fit connections are the types of interference fit connections described in the different configurations of the two connection embodiment 400 and described in the descriptions of the other embodiments of the modular implant, other interference fit connections such as shrink fit, expansion fit, and cam lock fit are also commonly used in the mechanical connection of parts and can be adapted for use in embodiments of the modular implant for joint reconstruction.

As described briefly above, shrink fit connections are accomplished by applying a force to the female component that causes the bore of the female component to shrink to a dimension that is smaller than the male component. This force is the result of the thermal expansion characteristic of the female component material. The shrink fit is generated by first heating the female component to a temperature above its working temperature, then assembling the male and female components together allowing them to cool. This results in the female component shrinking back to the dimension in which its bore is smaller than that of the male component exterior. This dimensional interference results in an interference fit between the two components. Other methods of applying a contracting force to the female component are also applicable such as: inducing a material change that results in a contraction as in the case of dehydrating the female component, removing a radially constraining element from the female component that allows residual compressive forces within the female component to relax resulting in internal radial contraction, manufacturing the female component from a material that undergoes a phase transformation when a magnetic flux is applied as in the case for magnetostrictive materials such as Terfenol, or heat is applied as is the case for shape memory materials such as Nitinol, or an electric current is applied or removed such as in piezoelectric materials.

As briefly described above, expansion fits are interference fits that are accomplished by applying an expansion force to the male component. This is done by cooling the male component, inserting it into the female component, and then allowing the component heat back to its working temperature. This results in an interference fit between the two components. Other methods of applying an expansion force to the male component are also applicable such as: manufacturing the male component from a material that undergoes a phase transformation resulting in linear contraction and radial expansion, or releasing a constraining element from the male component that results in allowing the male component to radially expand. An expansion fit can also be obtained by inserting a male component that is linearly stretched and radially contracted, due to the Poison effect of the material. Then, after insertion, releasing the constraining force keeping the male component stretched to allow the male component to radially expand.

A cam lock interference fit is accomplished by designing the cross-section of the exterior surface of the male component and the cross-section of the internal surface of the female in a like non-circular shape. The components are slipped together, and then rotated with respect to each other to generate a cam lock effect locking the two components together.

Various assembly methods are applicable when assembling the two-connection embodiment 400 of the modular implant 10 during surgery. The method, which the surgeon chooses to employ, is dependent on the specific anatomy of the patient.

In a first assembly method embodiment of the two-connection embodiment, the mated stem 40 and base 20 are configured to pass into the internal bore 34 of the body 30, and the interference fit connector 22 of the base 20 mates with the internal bore 34 of the body 30. This allows the surgeon to place the body 30 in the bone, and then place the assembled base 20 and stem 40 through the body 30. In this first assembly method embodiment of the two-connection embodiment 400 of the modular implant 10, the stem 40 and the body 30 do not share connection surfaces that mate directly with each other after final assembly. In the case of the two-connection embodiment 400, the interference fit connector 45 of the stem 40 mates with an internal channel 24 of the base 20 during assembly and in use.

In a second assembly method embodiment of the two-connection embodiment 400, the stem 40 is first placed in the bone, followed by the body 30, followed by the base 20. The base 20, body 30 and stem 40 are then aligned and locked together.

In a third assembly method embodiment of the two-connection embodiment 400, first the stem 40 is placed in the bone, second the body 30 and the base 20 are assembled outside of the bone, then the assembled body 30 and base 20 are placed in the bone together and assembled with the stem 40.

As previously mentioned, the objective of a successful modular implant design is to provide the surgeon with a wide range of surgical options, limit the inventory on hand, and provide mating technology between the components that allows for a functional and practical assembly process resulting in strong mechanical bonds between the components.

Figure 7:
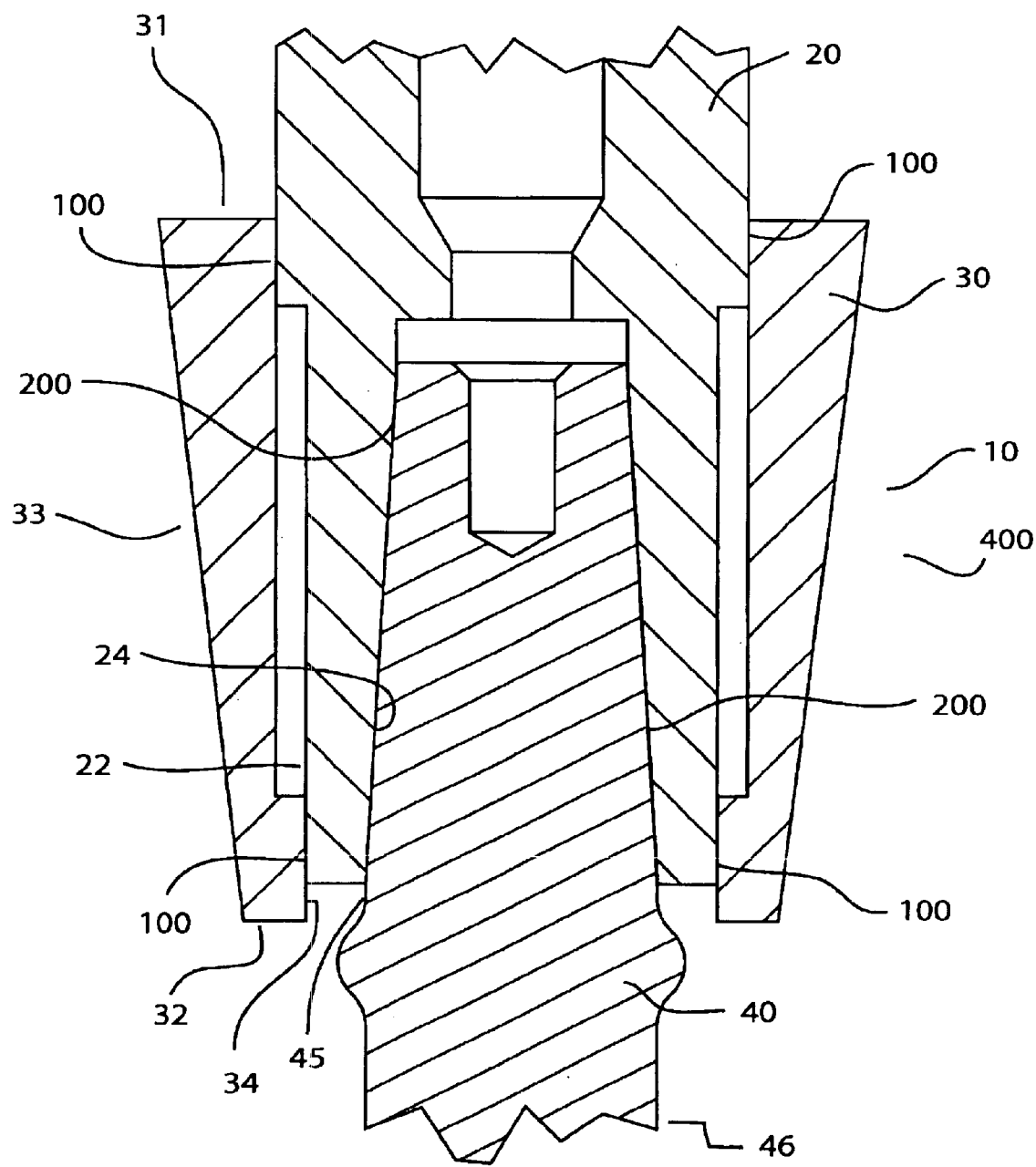
FIG. 7 is a close-up cross-sectional view of the connections between the components of a two-connection embodiment of the modular implant showing a tapered interference fit connection between the base and the stem and a multiple zone press fit interference fit connection between the base and the body.

Referring to FIG. 7, a close-up cross-sectional view is shown of the connections between the components of a two-connection embodiment of the modular implant. Between the base 20 and the body 30 the first connection 100 is shown as a multiple zone press fit, and between the base 20 and the stem 40 the second connection 200 is shown as a tapered connection.

Figure 8:
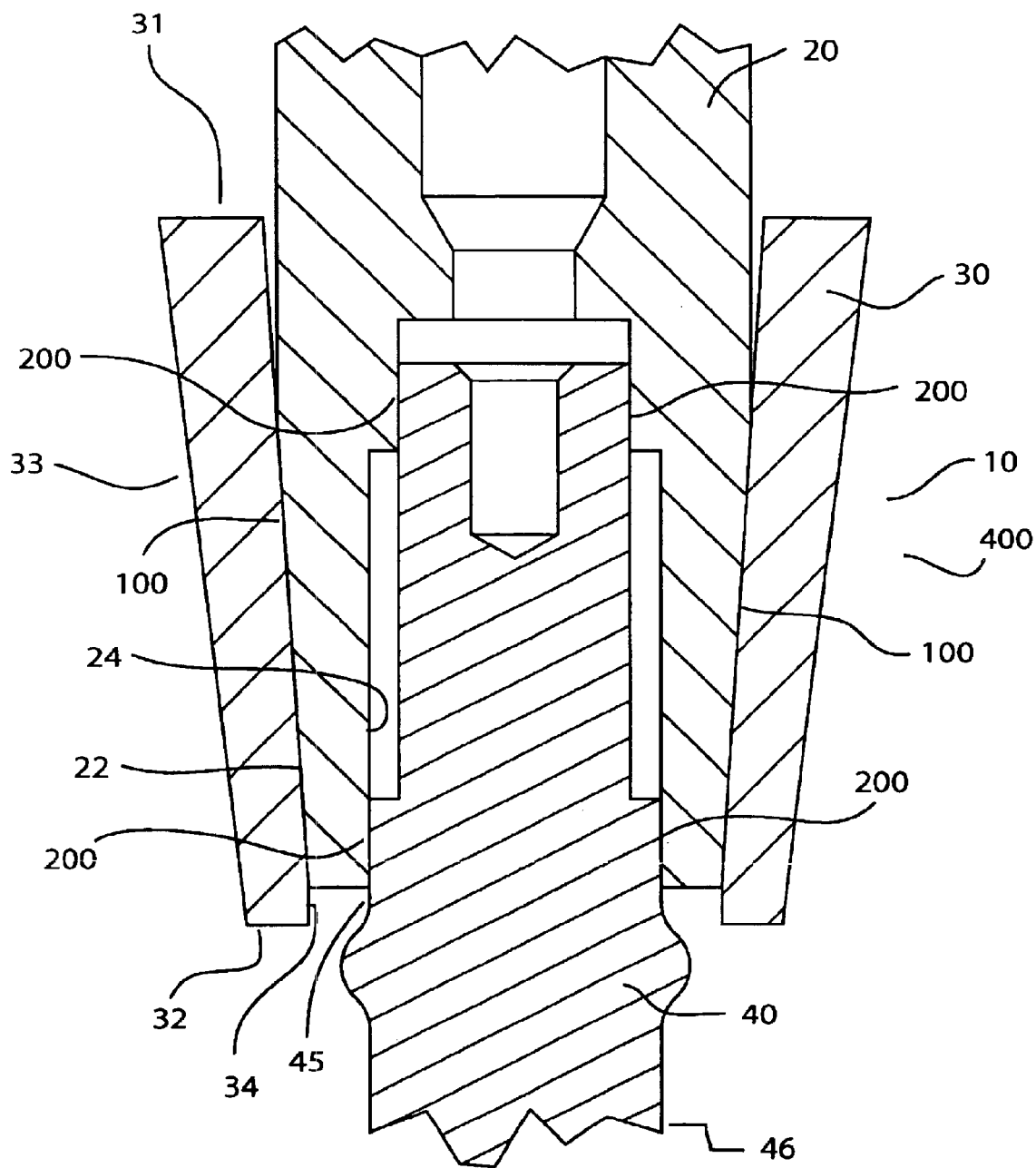
FIG. 8 is a close-up cross-sectional view of a two-connection embodiment of the modular implant showing a multiple zone press fit connection between the base and the stem and a tapered interference fit connection between the base and the body.

FIG. 8 is a close-up cross-sectional view of a two-connection embodiment of the modular implant. Between the base 20 and the body 30 the first connection 100 is a tapered connection, and between the base 20 and the stem 40 the second connection 200 is a multiple zone press fit connection.

Figure 9:
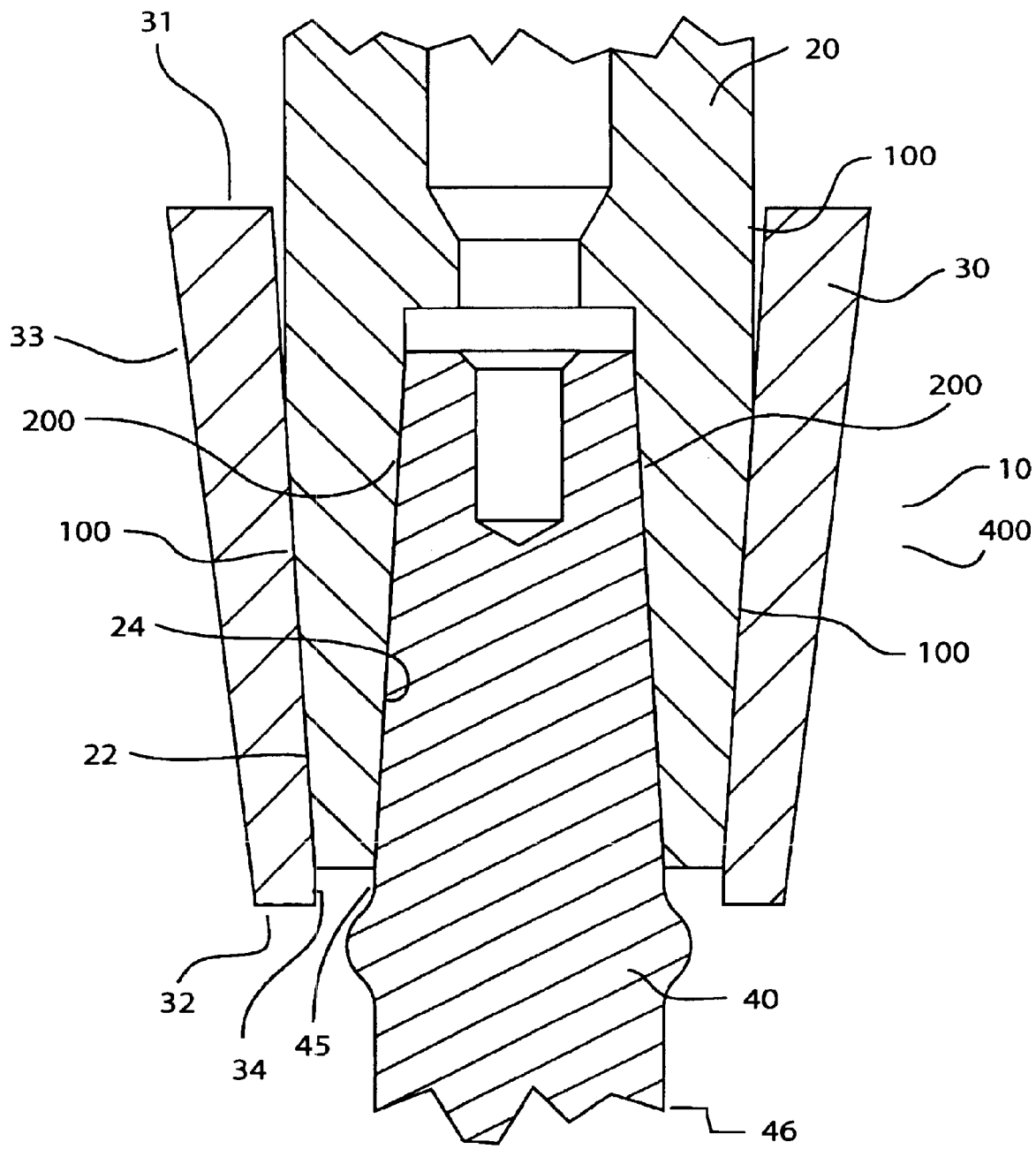
FIG. 9 is a close-up cross-sectional view of a two-connection embodiment of the modular implant showing a tapered connection between the base and the body and a tapered connection between the base and the stem.

Referring to FIG. 9, a close-up cross-sectional view is shown of a two-connection embodiment of the modular implant. Between the base 20 and the body 30 the first connection 100 is a tapered connection, and between the base 20 and the stem 40 the second connection 200 is a tapered connection.

Figure 10:
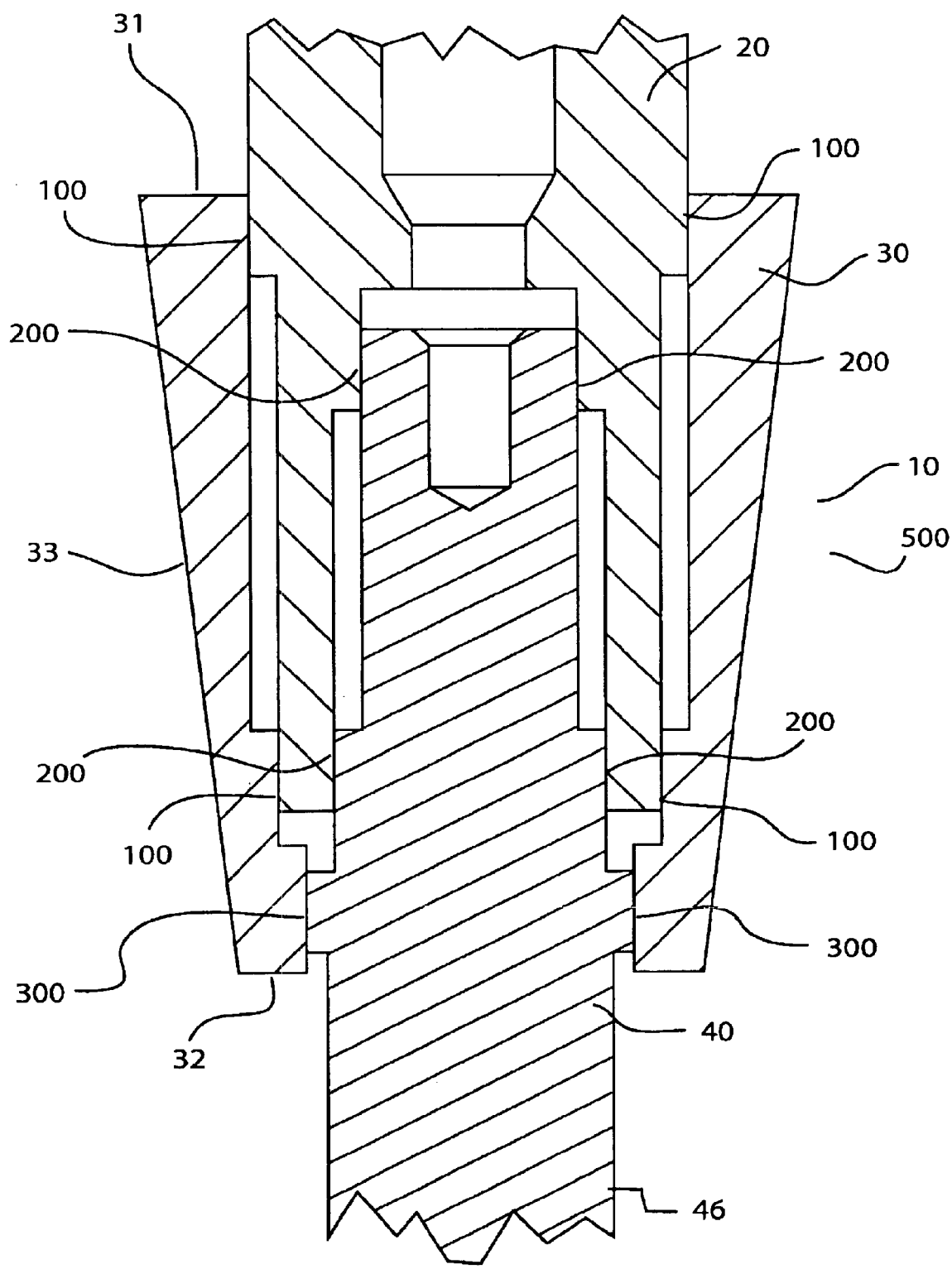
FIG. 10 is a close-up cross-sectional view of a three-connection embodiment of the modular implant showing a multiple zone press fit connection between the base and the body, a multiple zone press fit connection between the base and the stem, and a press fit connection between the body and the stem.

Referring to FIG. 10, a close-up cross-sectional view is shown of a three-connection embodiment of the modular implant. A three-connection embodiment 500 of the modular implant 10 is configured to allow three connection regions. The first connection 100 is between the body 30 and the base 20, the second connection 200 is between the base 20 and the stem 40, and the third connection 300 is between the stem 40 and the body 30. Between the base 20 and the body 30 the first connection 100 is a press fit connection. Between the base 20 and the stem 40 the second connection 200 is a multiple zone press fit connection. Between the body 30 and the stem 40 a third connection 300 is a press fit connection.

Figure 11:
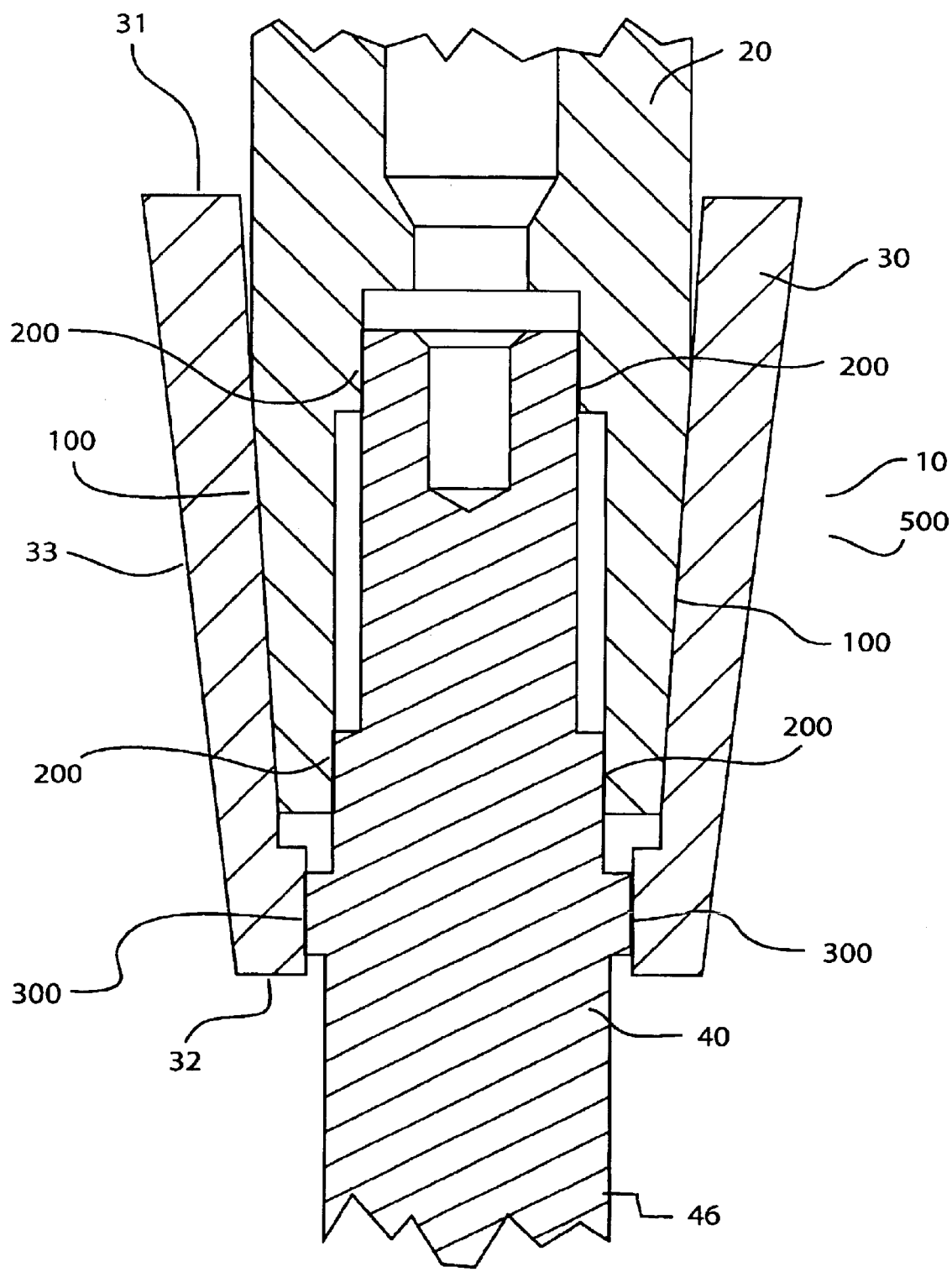
FIG. 11 is a close-up cross-sectional view of a three-connection embodiment of the modular implant showing a tapered connection between the base and the body, a multiple zone press fit connection between the base and the stem, and a press fit connection between the body and the stem.

Referring to FIG. 11, a close-up cross-sectional view is shown of the three-connection embodiment 500 of the modular implant 10. Between the base 20 and the body 30 the first connection 100 is a tapered connection. Between the base 20 and the stem 40 the second connection 200 is a multiple zone press fit connection. Between the body 30 and the stem 40 a third connection 300 is a press fit connection.

Figure 12:
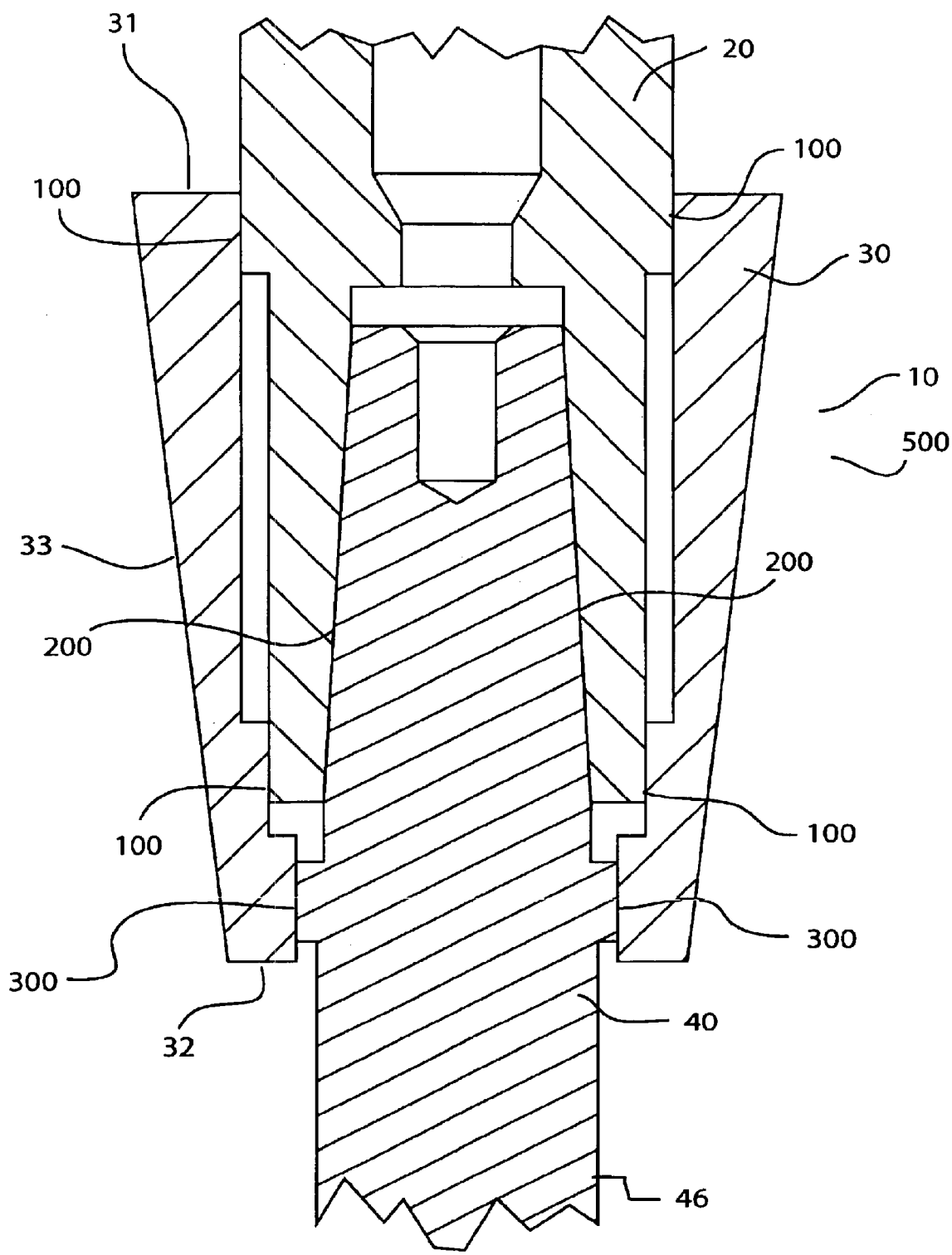
FIG. 12 is a close-up cross-sectional view of a three-connection embodiment of the modular implant showing a multiple zone press fit connection between the base and the body, a tapered connection between the base and the stem, and a press fit connection between the body and the stem.

Referring to FIG. 12, a close-up cross-sectional view is shown of the three-connection embodiment 500 of the modular implant 10. Between the base 20 and the body 30 the first connection 100 is a multiple-zone press fit connection. Between the base 20 and the stem 40 the second connection 200 is a tapered connection. Between the body 30 and the stem 40 a third connection 300 is a press fit connection.

Figure 13:
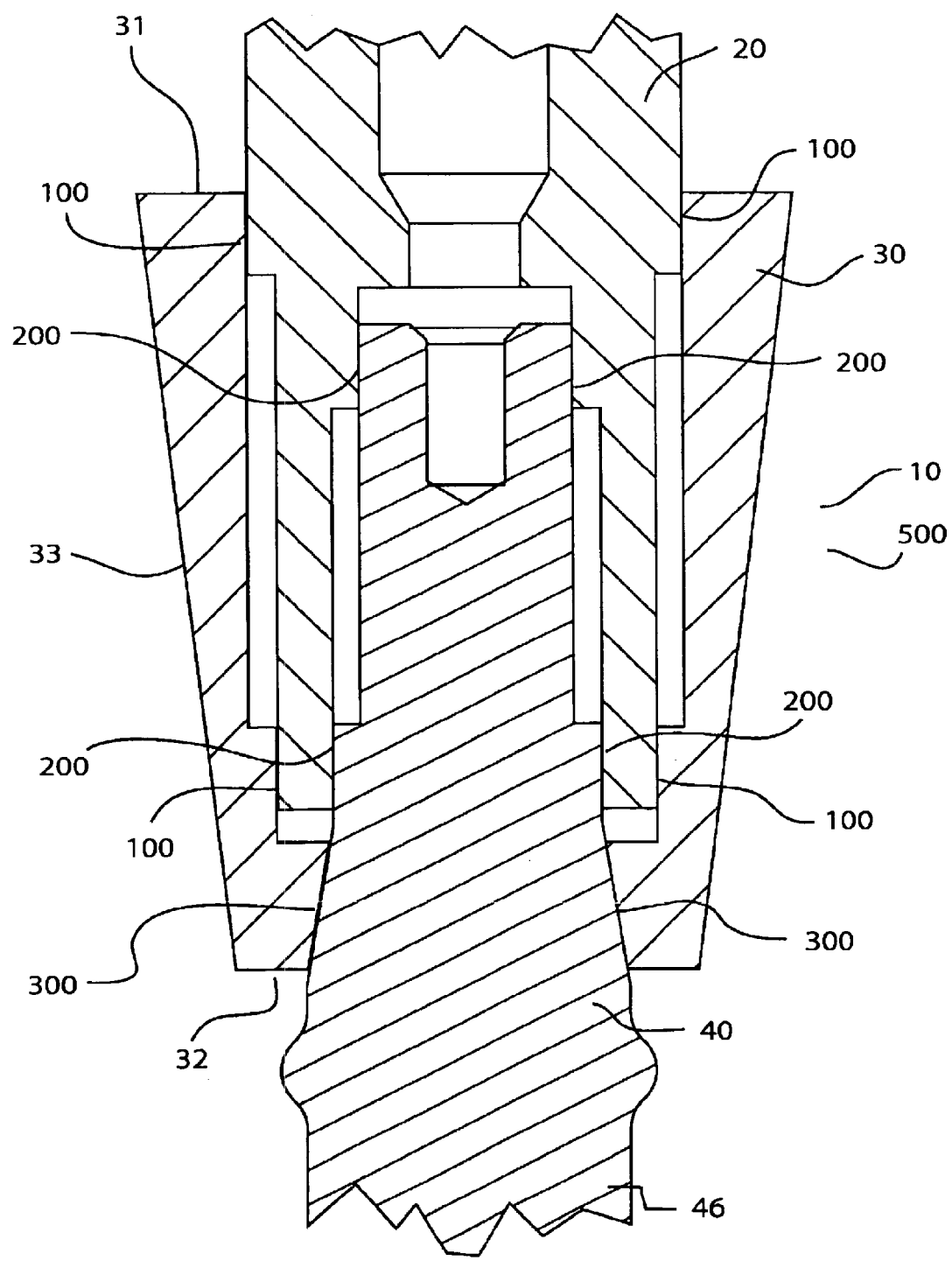
FIG. 13 is a close-up cross-sectional view of a three-connection embodiment of the modular implant showing a press fit connection between the base and the body, a multiple zone press fit connection between the base and the stem, and a tapered connection between the body and the stem.

Referring to FIG. 13, a close-up cross-sectional view is shown of the three-connection embodiment 500 of the modular implant 10. Between the base 20 and the body 30 the first connection 100 is a multiple-zone press fit connection. Between the base 20 and the stem 40 the second connection 200 is a multiple-zone press fit connection. Between the body 30 and the stem 40 a third connection 300 is a tapered connection.

Figure 14:
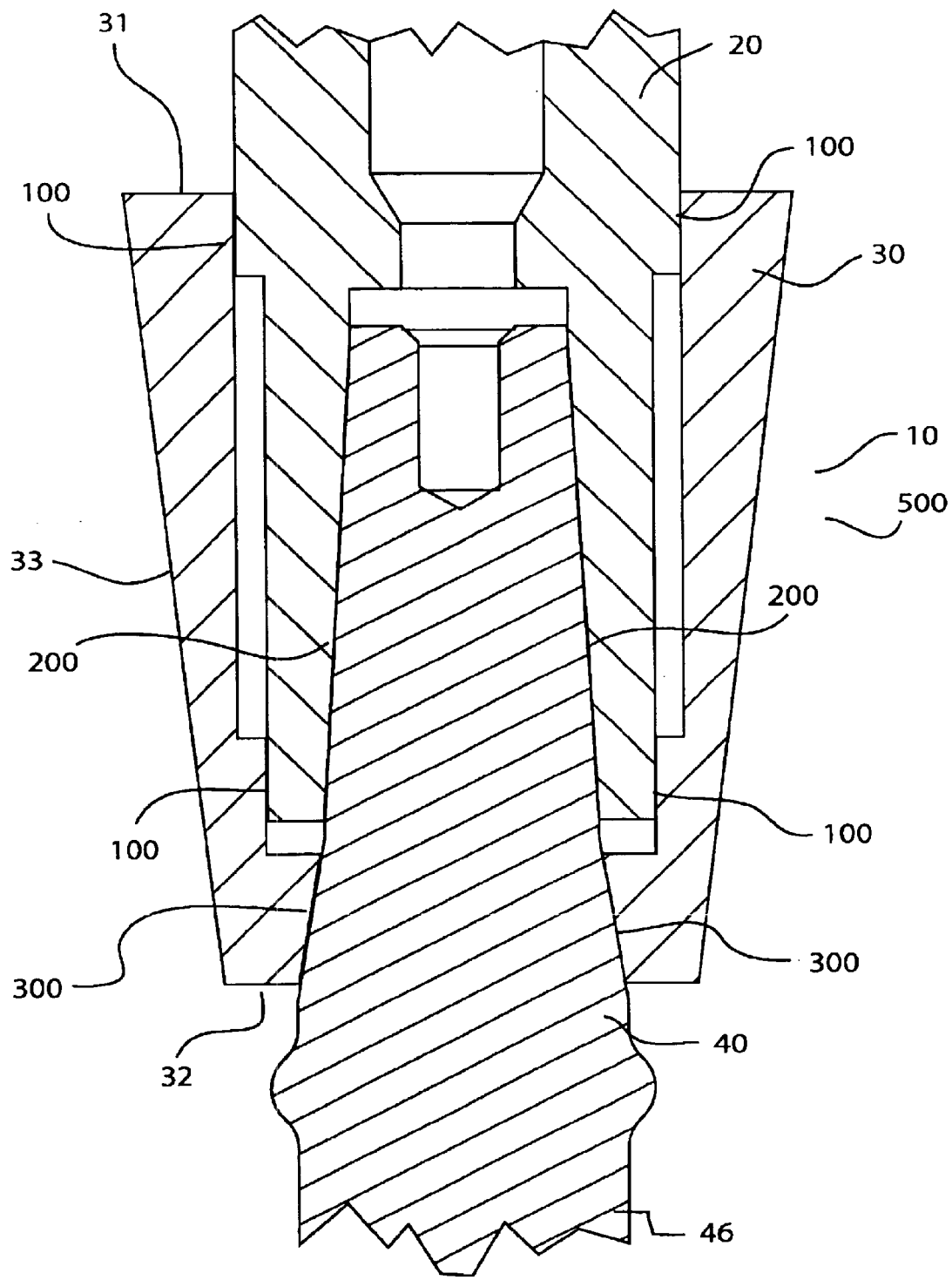
FIG. 14 is a close-up cross-sectional view of a three-connection embodiment of the modular implant showing a multiple zone press fit connection between the base and the body, a tapered connection between the base and the stem, and a tapered connection between the body and the stem.

Referring to FIG. 14, a close-up cross-sectional view is shown of the three-connection embodiment 500 of the modular implant 16. Between the base 20 and the body 30 the first connection 100 is a multiple-zone press fit connection. Between the base 20 and the stem 40 the second connection 200 is a tapered connection. Between the body 30 and the stem 40 a third connection 300 is a tapered connection.

Figure 15:
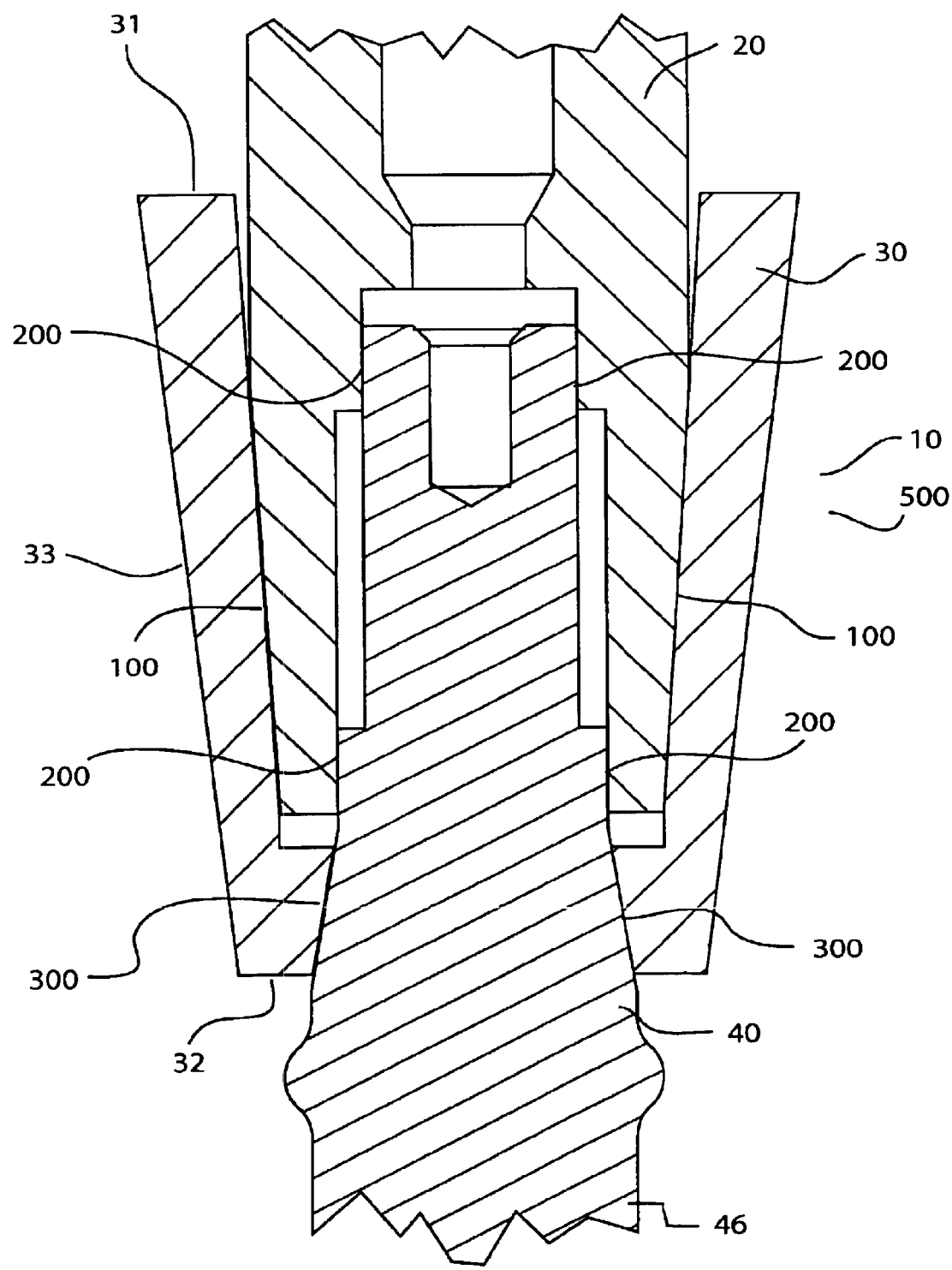
FIG. 15 is a close-up cross-sectional view of a three-connection embodiment of the modular implant showing a tapered connection between the base and the body, a multiple zone press fit connection between the base and the stem, and a tapered connection between the body and the stem.

Referring to FIG. 15, a close-up cross-sectional view is shown of the three-connection embodiment 500 of the modular implant 10. Between the base 20 and the body 30 the first connection 100 is a tapered connection. Between the base 20 and the stem 40 the second connection 200 is a multiple-zone press fit connection. Between the body 30 and the stem 40 a third connection 300 is a tapered connection.

Figure 16:
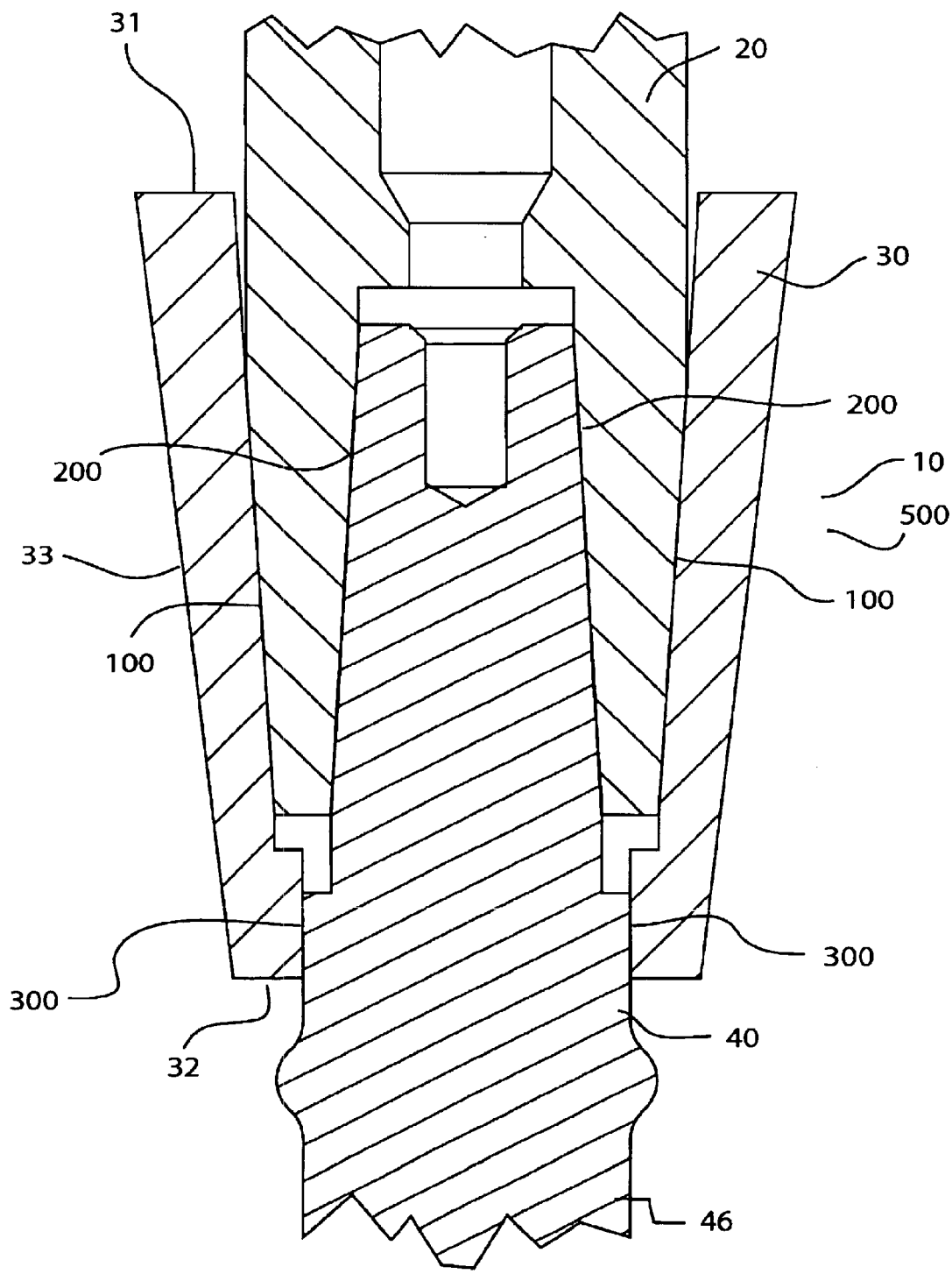
FIG. 16 is a close-up cross-sectional view of a three-connection embodiment of the modular implant showing a tapered connection between the base and the body, a tapered connection between the base and the stem, and a press fit connection between the body and the stem.

Referring to FIG. 16, a close-up cross-sectional view is shown of the three-connection embodiment 500 of the modular implant 10. Between the base 20 and the body 30 the first connection 100 is a tapered connection. Between the base 20 and the stem 40 the second connection 200 is a tapered connection. Between the body 30 and the stem 40 a third connection 300 is a press fit connection.

Figure 17:
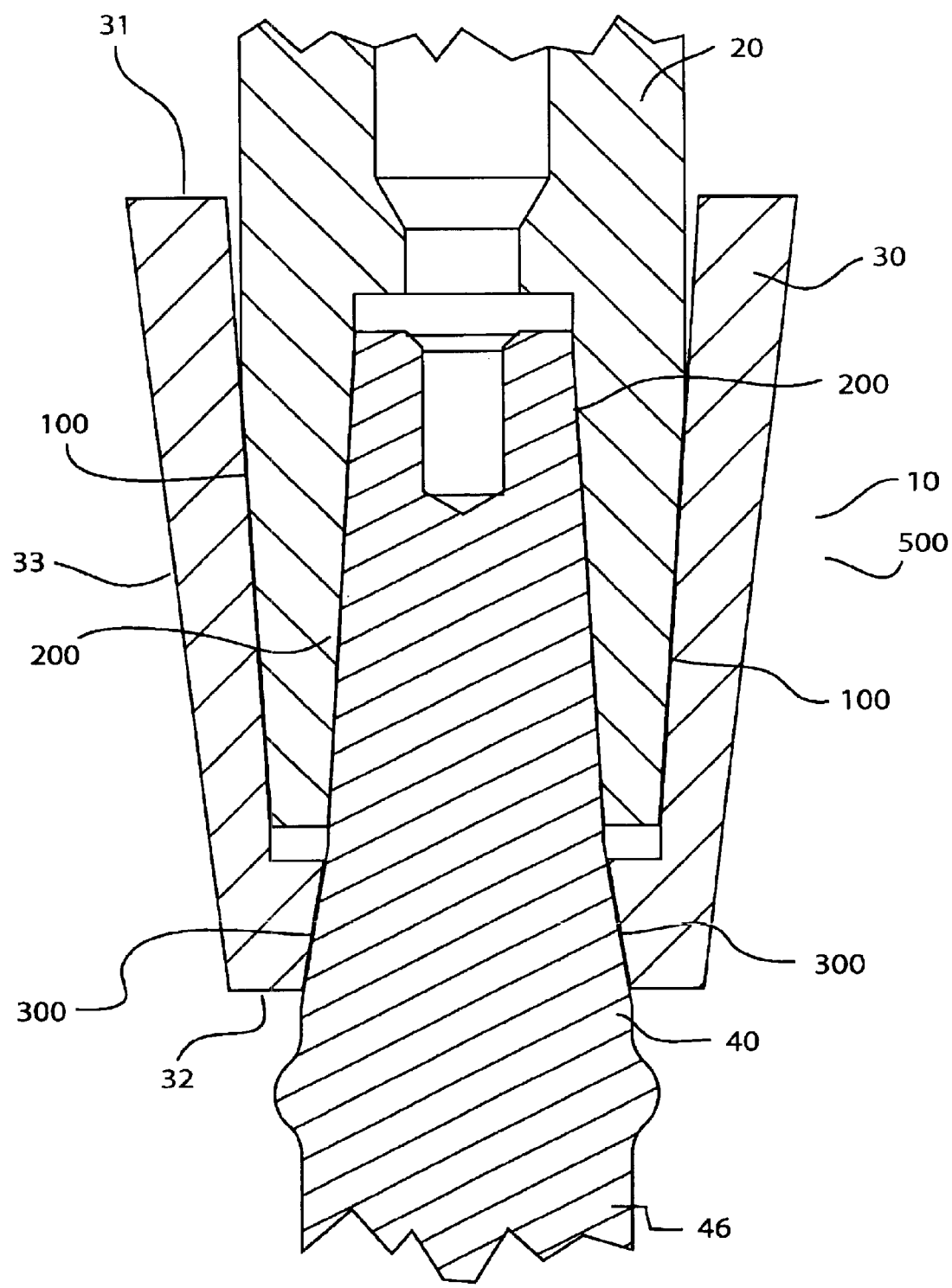
FIG. 17 is a close-up cross-sectional view of a three-connection embodiment of the modular implant showing a tapered connection between the base and the body, a tapered connection between the base and the stem, and a tapered connection between the boy and the stem.

Referring to FIG. 17, a close-up cross-sectional view is shown of the three-connection embodiment 500 of the modular implant 10. Between the base 20 and the body 30 the first connection 100 is a tapered connection. Between the base 20 and the stem 40 the second connection 200 is a tapered connection. Between the body 30 and the stem 40 a third connection 300 is a tapered connection.

Figure 18A:
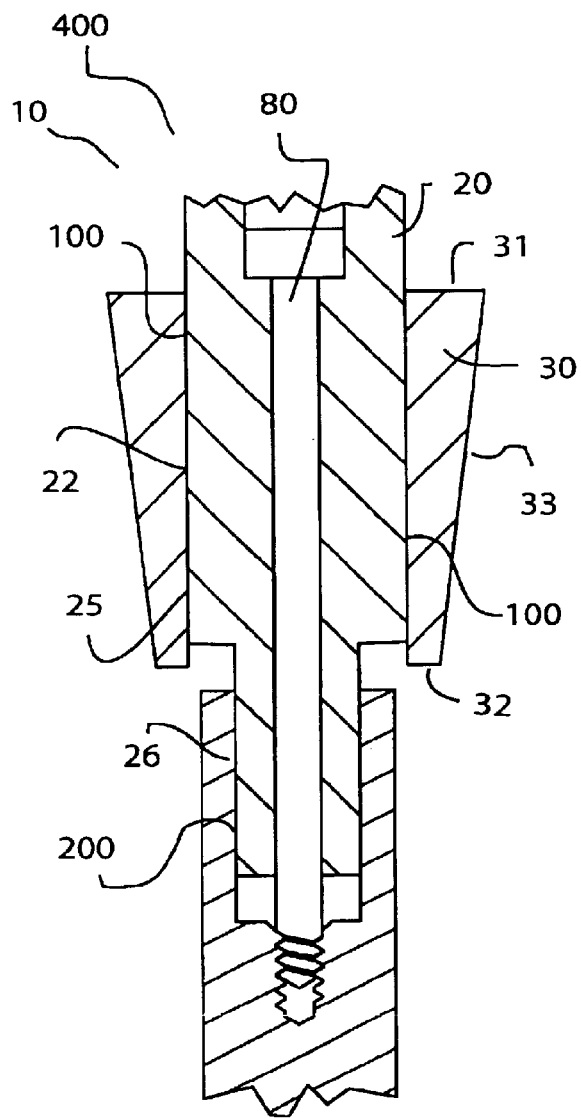
FIG. 18A is a close-up cross-sectional view of a two-connection embodiment of the modular implant showing an interference fit connector of the base having a first external surface and a second external surface, a press fit connection between the base and the body, a press fit connection between the base and the stem, and a securing element passing from the base and threading into the stem.

Referring to FIG. 18A, a close-up cross-sectional view is shown of a configuration of the two-connection embodiment 400 of the modular implant 10. This embodiment shows an interference fit connector 22 of the base 20 having a first external surface 25 and a second external surface 26. The first connection 100 between the base 20 and the body 30 and the second connection 200 between the base 20 and the stem 40 are shown as press fit connections. This embodiment also shows a securing element 80 passing from the base 20 and threading into the stem 40.

Figure 18B:
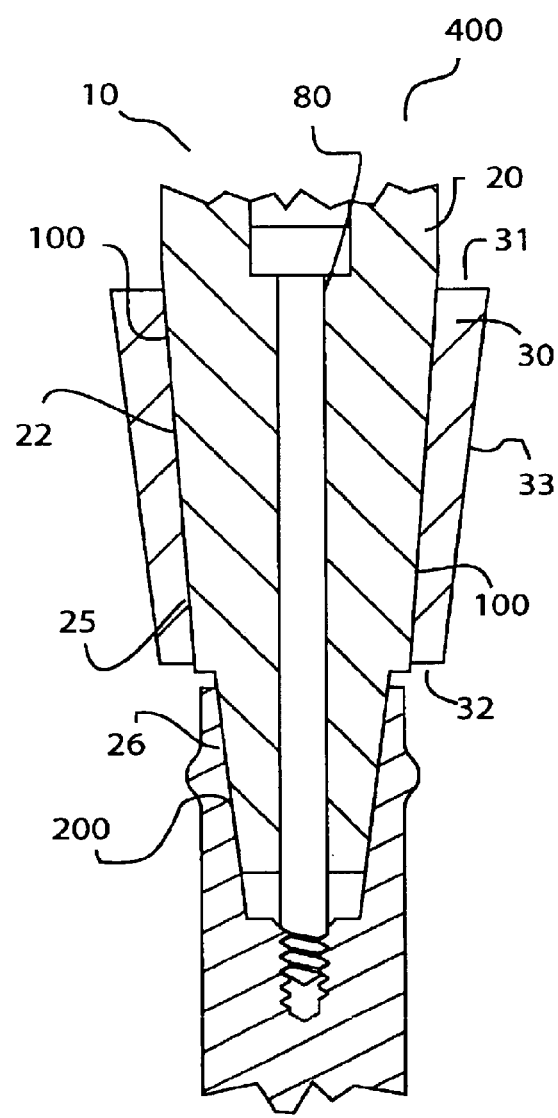
FIG. 18B is a close-up cross-sectional view of a two-connection embodiment of the modular implant showing an interference fit connector of the base having a first external surface and a second external surface, a tapered connection between the base and the body, a tapered connection between the base and the stem, and a securing element passing from the base and threading into the stem.

Referring to FIG. 18B, a close-up cross-sectional view is shown of a configuration of the two-connection embodiment 400 of the modular implant 10. This embodiment shows the interference fit connector 22 of the base 20 having the first external surface 25 and the second external surface 26. The first connection 100 between the base 20 and the body 30 and the second connection 200 between the base 20 and the stem 40 are shown as tapered connections. This embodiment also shows the securing element 80 passing from the base 20 and threading into the stem 40.

Figure 19A:
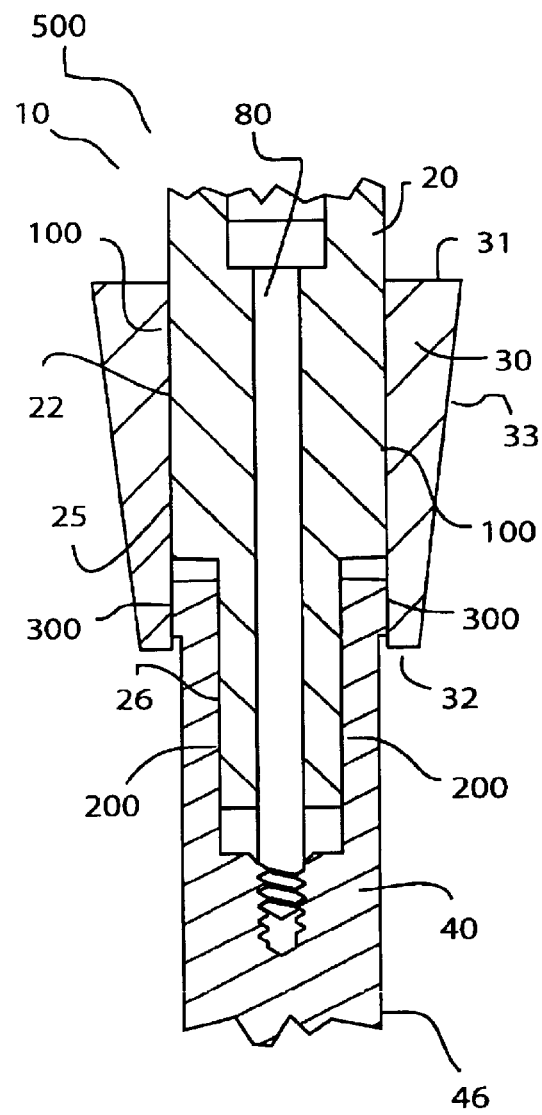
FIG. 19A is a close-up cross-sectional view of a three-connection embodiment of the modular implant showing an interference fit connector of the base having a first external surface and a second external surface, a press fit connection between the base and the body, a press fit connection between the base and the stem, a press fit connection between the body and the stem, and a securing element passing from the base and threading into the stem.

Referring to FIG. 19A, a close-up cross-sectional view is shown of a configuration of the three-connection embodiment 500 of the modular implant 10. This embodiment shows the interference fit connector 22 of the base 20 having the first external surface 25 and the second external surface 26. The first connection 100 between the base 20 and the body 30, the second connection between the base 20 and the stem 40 and the third connection 300 between the body 30 and the stem 40 are shown as press fit connections. This embodiment also shows the securing element 80 passing from the base 20 and threading into the stem 40.

Figure 19B:
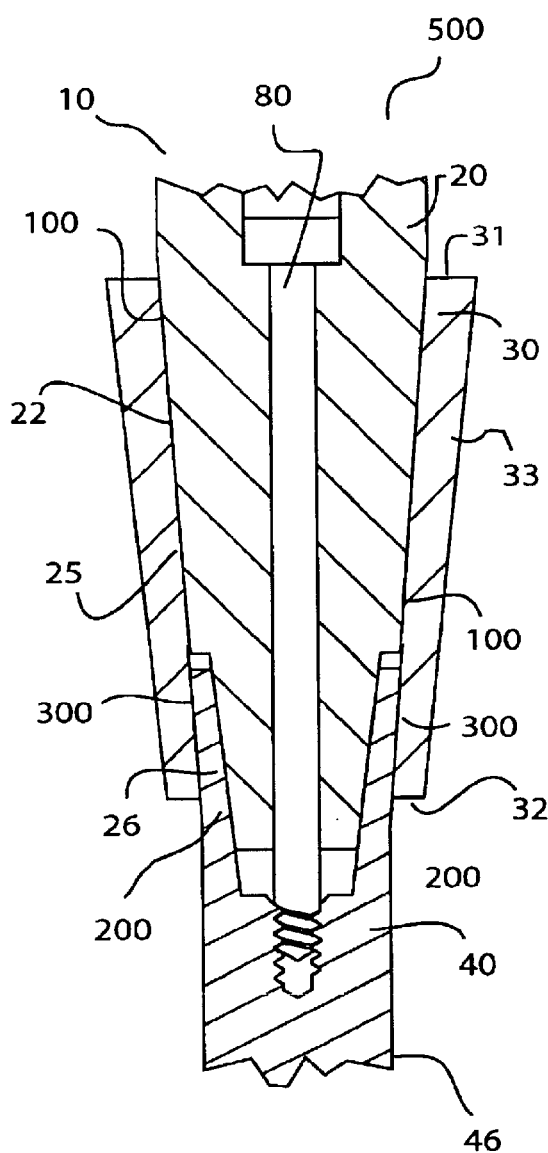
FIG. 19B is a close-up cross-sectional view of a three-connection embodiment of the modular implant showing an interference fit connector of the base having a first external surface and a second external surface, a tapered connection between the base and the body, a tapered connection between the base and the stem, a tapered connection between the body and the stem, and a securing element passing from the base and threading into the stem.

Referring to FIG. 19B, a close-up cross-sectional view is shown of a configuration of the three-connection embodiment 500 of the modular implant 10. This embodiment shows the interference fit connector 22 of the base 20 having the first external surface 25 and the second external surface 26. The first connection 100 between the base 20 and the body 30, the second connection 200 between the base 20 and the stem 40 and the third connection 300 between the body 30 and the stem 40 are shown as tapered connections. This embodiment also shows the securing element 80 passing from the base 20 and threading into the stem 40.

Figure 20A:
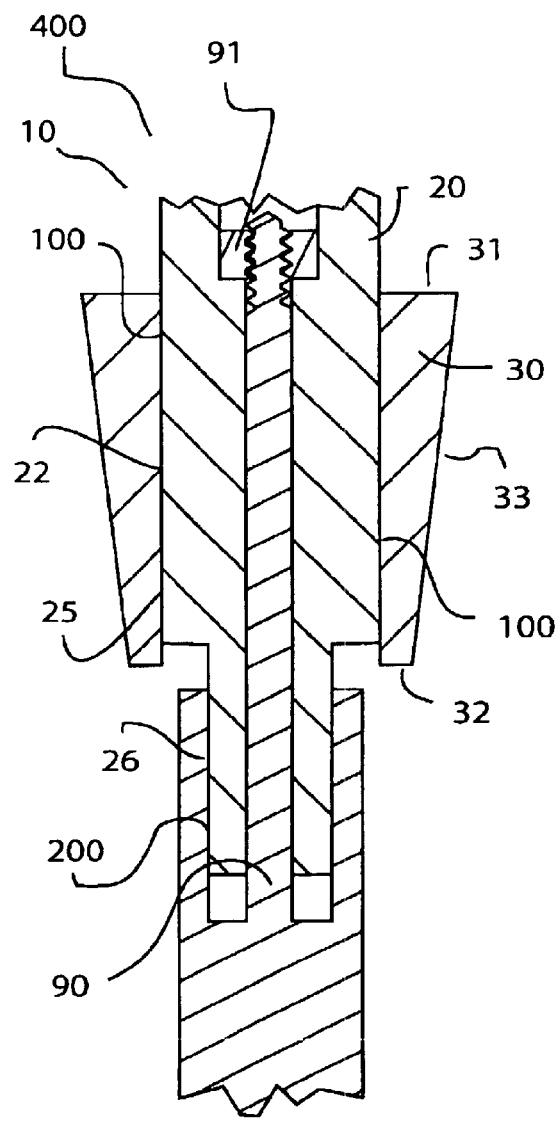
FIG. 20A is a close-up cross-sectional view of a two-connection embodiment of the modular implant showing an interference fit connector of the base having a first external surface and a second external surface, a press fit connection between the base and the body, a press fit connection between the base and the stem, and a securing element protrusion protruding from the stem and passing through the body and through the base to the first end of the base, with threads received by a securing fastener.

Referring to FIG. 20A, a close-up cross-sectional view is shown of a configuration of the two-connection embodiment 400 of the modular implant 10. This embodiment shows the interference fit connector 22 of the base 20 having the first external surface 25 and the second external surface 26. The first connection 100 between the base 20 and the body 30 and the second connection 200 between the base 20 and the stem 40 are shown as press fit connections. This embodiment also shows a securing element protrusion 90 protruding from the stem 40 and passing through the body 30 and through the base 20 to the first end 21 of the base 20, and threading into a securing fastener 91.

Figure 20B:
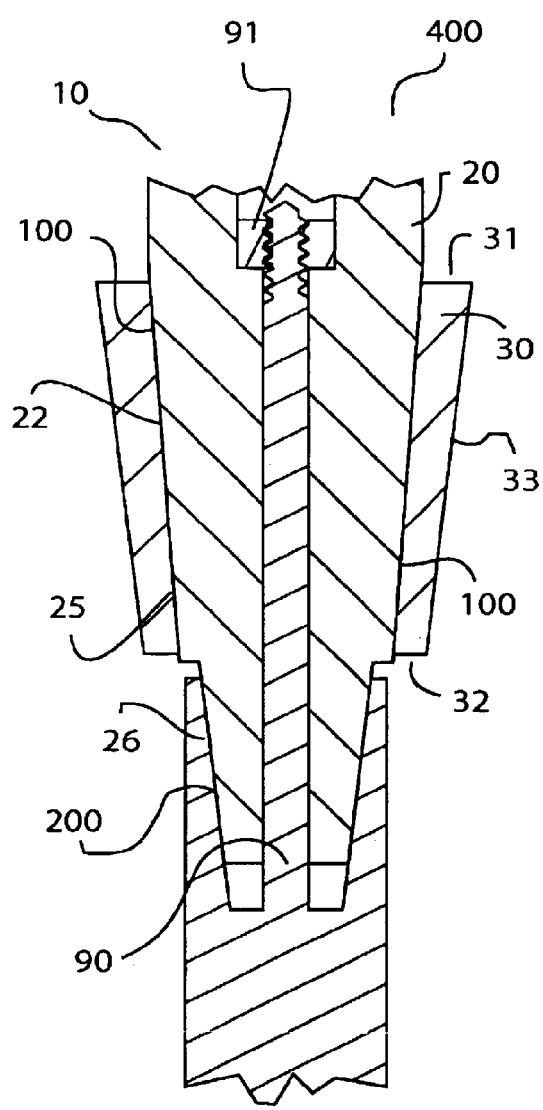
FIG. 20B is a close-up cross-sectional view of a two-connection embodiment of the modular implant showing an interference fit connector of the base having a first external surface and a second external surface, a tapered connection between the base and the body, a tapered connection between the base and the stem, and a securing element protrusion protruding from the stem and passing through the body and through the base to the first end of the base, with threads received by a securing fastener.

Referring to FIG. 20B, a close-up cross-sectional view is shown of a configuration of the two-connection embodiment 400 of the modular implant 10. This embodiment shows the interference fit connector 22 of the base 20 having the first external surface 25 and the second external surface 26. The first connection 100 between the base 20 and the body 30 and the second connection 200 between the base 20 and the stem 40 are shown as tapered connections. This embodiment also shows the securing element protrusion 90 protruding from the stem 40 and passing through the body 30 and through the base 20 to the first end 21 of the base 20, and threading into the securing fastener 91.

Figure 21A:
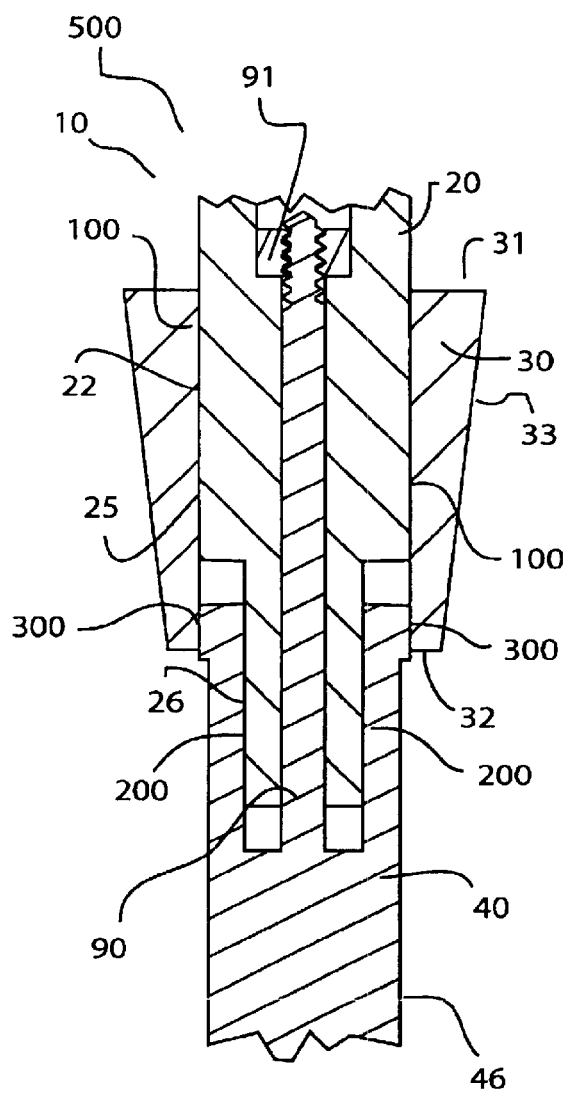
FIG. 21A is a close-up cross-sectional view of a three-connection embodiment of the modular implant showing an interference fit connector of the base having a first external surface and a second external surface, a press fit connection between the base and the body, a press fit connection between the base and the stem, a press fit connection between the body and the stem, and a securing element protrusion protruding from the stem and passing through the body and through the base to the first end of the base, with threads received by a securing fastener.

Referring to FIG. 21A, a close-up cross-sectional view is shown of a configuration of the three-connection embodiment 500 of the modular implant 10. This embodiment shows the interference fit connector 22 of the base 20 having the first external surface 25 and the second external surface 26. The first connection 100 between the base 20 and the body 30, the second connection 200 between the base 20 and the stem 40 and the third connection 300 between the body 30 and the stem 40 are shown as press fit connections. This embodiment also shows the securing element protrusion 90 protruding from the stem 40 and passing through the body 30 and through the base 20 to the first end 21 of the base 20, and threading into the securing fastener 91.

Figure 21B:
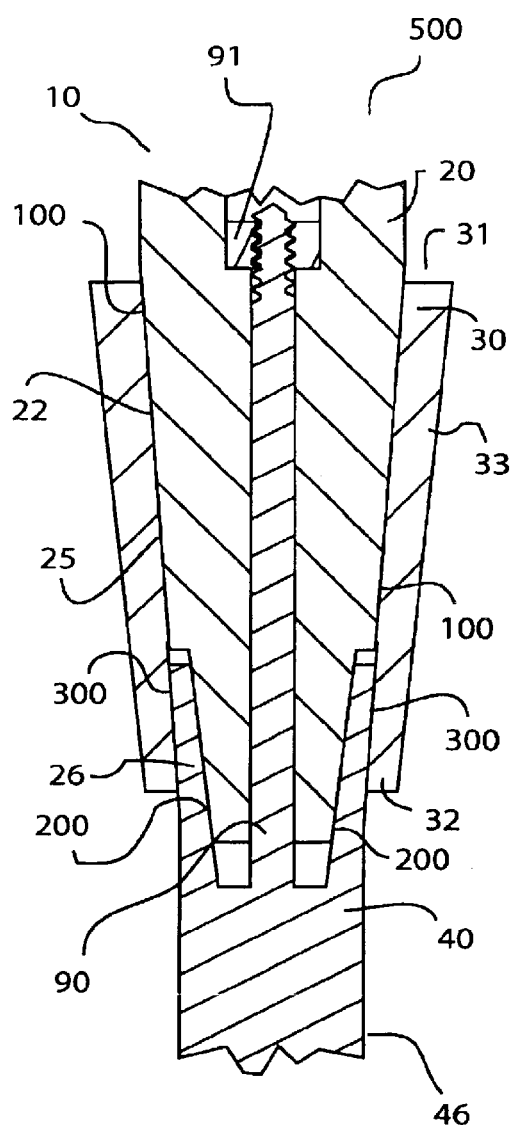
FIG. 21B is a close-up cross-sectional view of a three-connection embodiment of the modular implant showing an interference fit connector of the base having a first external surface and a second external surface, a tapered connection between the base and the body, a tapered connection between the base and the stem, and a tapered connection between the body and the stem, and a securing element protrusion protruding from the stem and passing through the body and through the base to the first end of the base, with threads received by a securing fastener.

Referring to FIG. 21B, a close-up cross-sectional view is shown of a configuration of the three-connection embodiment 500 of the modular implant 10. This embodiment shows the interference fit connector 22 of the base 20 having the first external surface 25 and the second external surface 26. The first connection 100 between the base 20 and the body 30, the second connection 200 between the base 20 and the stem 40 and the third connection 300 between the body 30 and the stem 40 are shown as tapered connections. This embodiment also shows the securing element protrusion 90 protruding from the stem 40 and passing through the body 30 and through the base 20 to the first end 21 of the base 20, and threading into the securing fastener 91.

Referring to FIG. 22A, a close-up cross-sectional view is shown of a configuration of the two-connection embodiment 400 of the modular implant 10. The first connection 100 between the base 20 and the body 30 and the second connection 200 between the base 20 and the stem 40 are shown as press fit connections. This embodiment also shows the securing element protrusion 90 protruding from the stem 40 and passing through the body 30 and through the base 20 to the first end 21 of the base 20, and threading into the securing fastener 91.

Referring to FIG. 22B, a close-up cross-sectional view is shown of a configuration of the two-connection embodiment 400 of the modular implant 10. The first connection 100 between the base 20 and the body 30 and the second connection between the base 20 and the stem 40 are shown as tapered connections. This embodiment also shows the securing element protrusion 90 protruding from the stem 40 and passing through the body 30 and through the base 20 to the first end 21 of the base 20, and threading into the securing fastener 91.

Figure 23A:
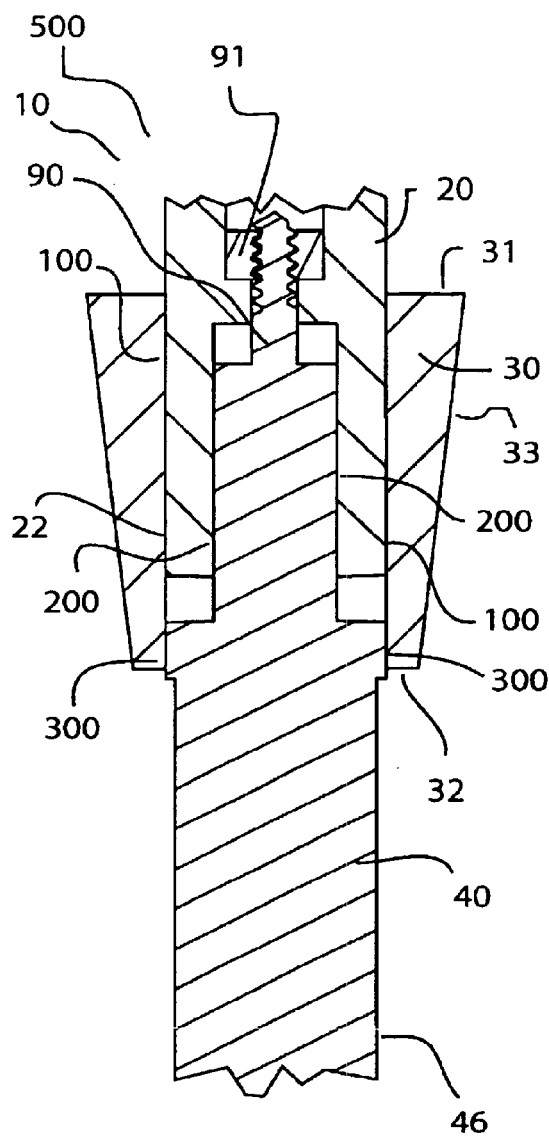
FIG. 23A is a close-up cross-sectional view of a three-connection embodiment of the modular implant showing a press fit connection between the base and the body, a press fit connection between the base and the stem, a press fit connection between the body and the stem, and a securing element protrusion protruding from the stem and passing through the body and through the base to the first end of the base, with threads received by a securing fastener.

Referring to FIG. 23A, a close-up cross-sectional view is shown of a configuration of the three-connection embodiment 500 of the modular implant 10. The first connection 100 between the base 20 and the body 30, the second connection 200 between the base 20 and the stem 40 and the third connection 300 between the body 30 and the stem 40 are shown as press fit connections. This embodiment also shows a securing element protrusion 90 protruding from the stem 40 and passing through the body 30 and through the base 20 to the first end 21 of the base 20, and threading into the securing fastener 91.

Figure 23B:
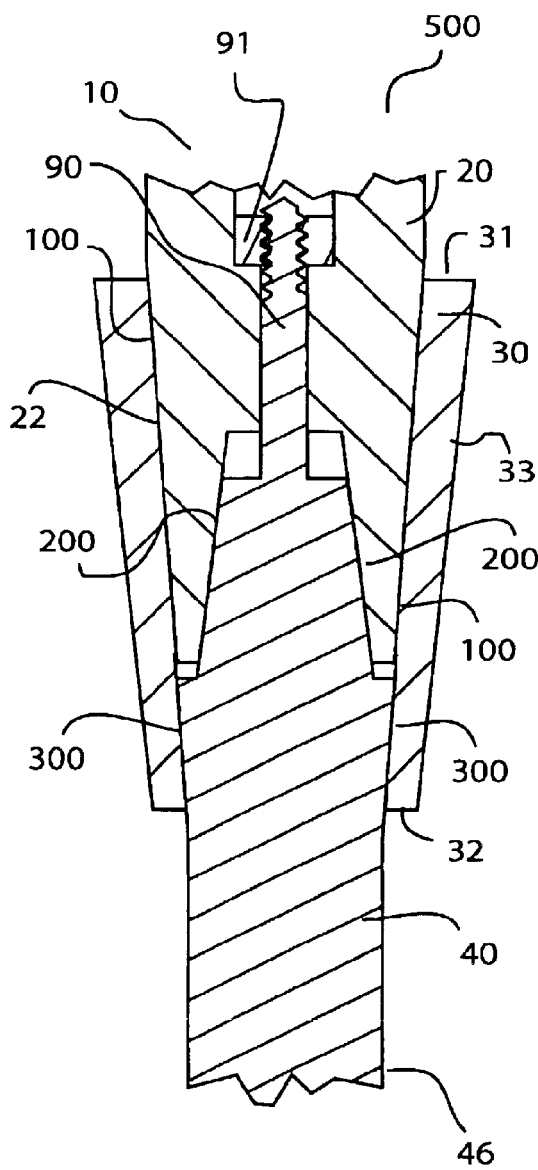
FIG. 23B is a close-up cross-sectional view of a three-connection embodiment of the modular implant showing a tapered connection between the base and the body, a tapered connection between the base and the stem, a tapered connection between the body and the stem, and a securing element protrusion protruding from the stem and passing through the body and through the base to the first end of the base, with threads received by a securing fastener.

Referring to FIG. 23B, a close-up cross-sectional view is shown of a configuration of the three-connection embodiment 500 of the modular implant. The first connection 100 between the base 20 and the body 30, the second connection 200 between the base 20 and the stem 40 and the third connection 300 between the body 30 and the stem 40 are shown as tapered connections. This embodiment also shows a securing element protrusion 90 protruding from the stem 40 and passing through the body 30 to the first end of the base 20 from the base 20 and threading into a securing fastener 91.

Figure 24A:
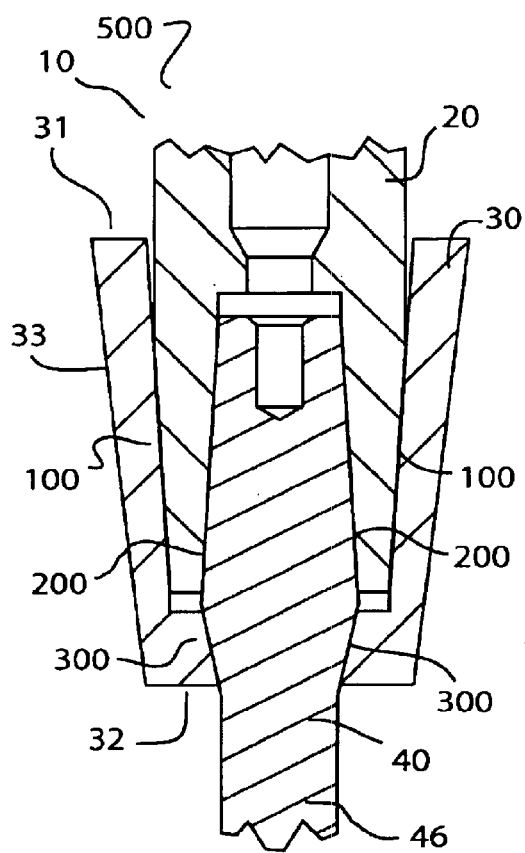
FIG. 24A is a close-up cross-sectional view of a three-connection embodiment of the modular implant showing tapered connection between the base and the body, a tapered connection between the base and the stem, and an tapered connection between the body and the stem.

Referring to FIG. 24A, a close-up cross-sectional view is shown of the three-connection embodiment 500 of the modular implant 10. Between the base 20 and the body 30 the first connection 100 is a tapered connection. Between the base 20 and the stem 40 the second connection 200 is a tapered connection. Between the body 30 and the stem 40 a third connection 300 is a tapered connection.

Figure 24B:
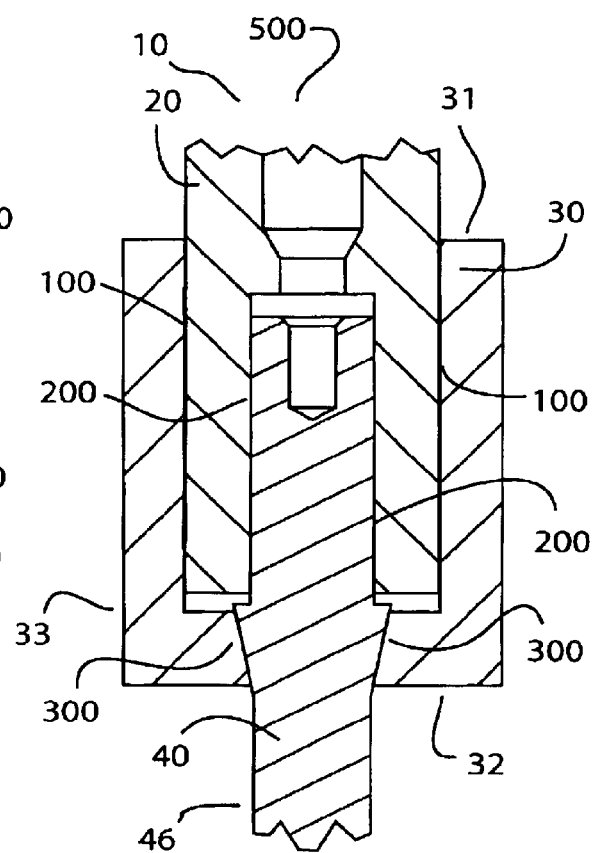
FIG. 24B is a close-up cross-sectional view of a three-connection embodiment of the modular implant showing a press fit connection between the base and the body, a press fit connection between the base and the stem, and a tapered connection between the body and the stem.

Referring to FIG. 24B, a close-up cross-sectional view is shown of the three-connection embodiment 500 of the modular implant 10. Between the base 20 and the body 30 the first connection 100 is a press fit connection. Between the base 20 and the stem 40 the second connection 200 is a press fit connection. Between the body 30 and the stem 40 a third connection 300 is a tapered connection.

Once selected, the prosthesis components may be assembled inside the patient in the order that suits the surgeon's surgical approach. The components may also be assembled outside the patient and then placed in the patient once assembled. Alternatively, some components of the assembly can be assembled outside the patient, then connected to the remaining component or components by assembly inside the patient.

While the present invention has been disclosed in its preferred form, the specific embodiments thereof as disclosed and illustrated herein are not to be considered in a limiting sense, as numerous variations are possible. The invention may be embodied in other specific forms without departing from its spirit or essential characteristics. The described embodiments are to be considered in all respects only as illustrative and not restrictive. No single feature, function, element or property of the disclosed embodiments is essential. The scope of the invention is, therefore, indicated by the appended claims rather than by the foregoing description. The following claims define certain combinations and subcombinations that are regarded as novel and non-obvious. Other combinations and subcombinations of features, functions, elements and/or properties may be claimed through amendment of the present claims or presentation of new claims in this or related applications. Such claims, whether they are broader, narrower or equal in scope to the original claims, are also regarded as included within the subject matter of applicant's invention. All changes that come within the meaning and range of equivalency of the claims are to be embraced within their scope.

What is claimed is:

1. A modular orthopedic implant comprising:
a tubular body with a top end, a bottom end, a tissue engaging external portion between the top end and the bottom end, and an internal bore passing through the top end and through the bottom end;
a base configured to receive an articulating portion on a first end and having an interference fit connector on a second end;
a stem with a elongated shaft configured to be situated inside of a bone, and a top end having an interference fit connector, wherein the interference fit connector of the stem mates with the interference fit connector of the base, the mated stem and base are insertable, in a mated configuration, into the internal bore of the body, and the interference fit connector of the base mates with the internal bore of the body.

2. An implant as recited in claim 1 wherein the interference fit connector of the base has an exterior surface and an internal channel.

3. An implant as recited in claim 2 wherein the external surface of the base and the internal bore of the body are configured to mate to form a press fit connection.

4. An implant as recited in claim 3 wherein the press fit connection is a multiple zone press fit connection.

5. An implant as recited in claim 3 or claim 4 wherein the internal channel of the base and the interference fit connector of the stem are configured to mate to form a tapered fit connection.

6. An implant as recited in claim 2 wherein the internal channel of the base and the interference fit connector of the stem are configured to mate to form a press fit connection.

7. An implant as recited in claim 6 wherein the press fit connection is a multiple zone press fit connection.

8. An implant as recited in claim 7 wherein the external surface of the base and the internal bore of the body are configured to mate to form a press fit connection.

9. An implant as recited in claim 8 wherein the press fit connection between the external surface and the internal bore of the body is a multiple zone press fit connection.

10. An implant as recited in claim 6 wherein the external surface of the base and the internal bore of the body are configured to mate to form a press fit connection.

11. An implant as recited in claim 10 wherein the press fit connection between the external surface and the internal bore of the body is a multiple zone press fit connection.

12. An implant as recited in claim 2 wherein the external surface of the base and the internal bore of the body are configured to mate to form a tapered fit connection.

13. An implant as recited in claim 12 wherein the internal channel of the base and the interference fit connector of the stem are configured to mate to form a tapered fit connection.

14. An implant as recited in claim 2 wherein the internal channel of the base and the interference fit connector of the stem are configured to mate to form a tapered fit connection.

15. An implant as recited in claim 14 wherein the external surface of the base and the internal bore of the body are configured to mate to form a tapered fit connection.

16. An implant as recited in claim 1 further comprising a securing element engaged with the top end of the stem, extending through the internal bore of the body, and connecting to the base, wherein the securing element secures the orientation of the base, body, and stem.

17. An implant as recited in claim 16 wherein the securing element is threaded into the stem.

18. An implant as recited in claim 1 wherein a securing element comprises a securing extension that protrudes from the top of the stem, through the internal bore of the body and through the base, and a securing fastener that is tightened onto the securing extension.

19. An implant as recited in claim 1 wherein the any of the interference fit connectors described are configured to function as shrink fit connections.

20. An implant as recited in claim 1 wherein the any of the interference fit connectors described are configured to function as expansion fit connectors.

21. An implant as recited in claim 1 wherein the any of the interference fit connectors described are configured to function as cam lock connectors.

22. A modular orthopedic implant comprising:
a tubular body with a top end, a bottom end, a tissue engaging external portion extending between the top end and the bottom end, and an internal bore passing through the top end and through the bottom end;
a base having a first end and a second end, the second end having an interference fit connector formed thereon;
a stem with a elongated shaft configured to be situated inside of a bone, and a top end having an interference fit connector, wherein the interference fit connector or the stem mates with the interference fit connector of the base, the mated stem and base are configured to pass into the internal bore of the body, and the interference fit connector of one of the stem and the base mates with the internal bore of the body independently of mating of the stem and base.

23. An implant as recited in claim 22 wherein the interference connector of the stem comprises an internal bore positioned in the top end, and the interference fit connector of the base has a first external surface configured to mate with the internal bore of the body and a second external surface configured to mate with the internal bore of the interference fit connector of the stem.

24. An implant as recited in claim 23 wherein a first external surface and the internal bore of the body are configured to mate to form a press fit connection.

25. An implant as recited in claim 24 wherein the press fit connection is a multiple zone press fit connection.

26. An implant as recited in claim 24 or claim 25 wherein the second external surface of the base and the internal bore of the stem are configured to mate to form a tapered fit connection.

27. An implant as recited in claim 23 wherein the second external surface of the base and the internal bore of the stem are configured to mate to form a press fit connection.

28. An implant as recited in claim 27 wherein the press fit connection is a multiple zone press fit connection.

29. An implant as recited in claim 27 or claim 28 wherein the first external surface and the internal bore of the body are configured to mate to form a press fit connection.

30. An implant as recited in claim 29 wherein the press fit connection between the first external surface and the internal bore of the body is a multiple zone press fit connection.

31. An implant as recited in claim 30 wherein the first external surface and the internal bore of the body are configured to mate to form a tapered fit connection.

32. An implant as recited in claim 29 wherein the second external surface of the base and the internal bore of the stem are configured to mate to form a tapered fit connection.

33. An implant as recited in claim 23 wherein the first external surface and the internal bore of the body are configured to mate to form a tapered fit connection.

34. An implant as recited in claim 23 wherein the second external surface of the base and the internal bore of the stem are configured to mate to form a tapered fit connection.

35. A method of assembling a modular orthopedic implant comprising:
   mating a body having a top end, bottom end, tissue engaging external portion between the top end and the bottom end, and an internal bore passing from the top end through the bottom end, to a base having a first end and an opposing second end that provides an articulating portion and a first connector being disposed at the first end; and
   mating the mated body and base to a stem having a elongated shaft on a first end and a connector on a second end such that at least one of the base and the stem is press fitted to the body along multiple axially separated locations.

36. A method of assembling a modular orthopedic implant as recited in claim 35 further comprising:
   rotationally orientating the body, base, and stem to optimize the fit inside of a bone cavity
   locking the body, base, and stem together by pulling on the stem and pushing on the base,
   securing the body, base, and stem connections and locking the orientation by tighten a securing element between the base and the stem.

37. A method of assembling a modular orthopedic implant comprising:
   providing
      a body having a top end, bottom end, tissue engaging external portion between the top end and the bottom end, and an internal bore passing from the top end through the bottom end;
      a base configured to provide an articulating portion on a first end and having an interference fit connector on a second end; and
      a stem with a long portion configured to be situated inside of a bone, and a top end having an interference fit connector; and
   mating the mated body and base to the stem by mating the interference fit connector of the stem to the interference fit connector of the base such that the stem is press fitted to the base along multiple axially separated locations.

38. A method of assembling a modular orthopedic implant comprising:
   providing
      a base configured to receive an articulating portion on a first end and having an interference fit connector on a second end,
      a body having a top end, bottom end, tissue engaging external portion between the top end and the bottom end, and an internal bore passing from the top end through the bottom end,
      a stem having a long portion configured to be situated inside of a bone, and a top end having an interference fit connector;
   mating the base to the stem, wherein the interference fit connector of the stem mates with the interference fit connector of the base and the mated stem and base are configured to pass into the internal bore of the body;
   mating the mated base and stem to the body, wherein, the interference fit connector of the base mates with the internal bore of the body.

39. A method of assembling a modular orthopedic implant comprising:
   mating a body having a top end, bottom end, tissue engaging external portion between the top end and the bottom end, and an internal bore passing from the top end through the bottom end, to a base configured to receive an articulating portion on a first end and having an interference fit connector on a second end;
   mating the mated body and base to a stem having a long portion configured to be situated inside of a bone, and an opposite end having an interference fit connection, wherein the interference fit connector of the stem mates with the interference fit connector of the base, the interference fit connector of the stem mates with the internal bore of the body and the internal bore of the body mates with the interference fit connector of the base.

40. A method of assembling a modular orthopedic implant as recited in claim 37, claim 38, or claim 39 further comprising:
   rotationally orientating the body, base, and stem to optimize the fit in an inside of a resected bone,
   locking the body, base, and stem together by pulling on the stem and pushing on the base,
   securing the body, base, and stem connections and locking in the orientation by tighten a securing element between the base and the stem.

41. A method of assembling a modular orthopedic implant comprising:
   mating a body having a top end, bottom end, tissue engaging external portion between the top end and the bottom end, and an internal bore passing from the top end through the bottom end, to a base configured to receive an articulating portion on a first end and having an interference fit connector on a second end;
   mating the mated body and base to a stem having a long portion configured to be situated inside of a bone, and an opposite end having an interference fit connection, wherein the interference fit connector of the stem mates with the interference fit connector of the base;
   rotationally orientating the body, base, and stem to optimize the fit in an inside of a resected bone,
   locking the body, base, and stem together by pulling on the stem and pushing on the base,
   securing the body, base, and stem connections and locking in the orientation by tighten a securing element between the base and the stem.

42. A modular orthopedic implant comprising:
   a tubular body having a top end, an opposing bottom end, and an interior surface bounding an internal bore extending therebetween, the internal bore having a maximum inner diameter;
   a base having a first end and an opposing second end, a first connector being disposed at the first end; and
   a stem comprising an elongated shaft having a second connector projecting therefrom, the stem having a maximum outer diameter smaller than the maximum inner diameter of the internal bore, the first connector mating with the second connector such that at least a portion of the mating is disposed within the internal bore of the tubular body, the first connector or second connector mating with the tubular body in an interference fit connection;
   wherein the any of the interference fit connectors described are configured to function as shrink fit connections.

43. An implant as recited in claim 42 wherein the base is configured to receive an articulating portion on a first end or wherein the base has an articulating portion formed on the first end.

44. An implant as recited in claim 42 wherein the interference fit connector of the base has an exterior surface and an internal channel.

45. An implant as recited in claim 44 wherein the external surface of the base and the internal channel of the body are configured to mate to form a press fit connection.

46. An implant as recited in claim 45 wherein the press fit connection is a multiple zone press fit connection.

47. An implant as recited in claim 45 or claim 46 wherein the internal channel of the base and the interference fit connector of the stem are configured to mate to form a tapered fit connection.

48. An implant as recited in claim 44 wherein the internal channel of the base and the interference fit connector of the stem are configured to mate to form a press fit connection.

49. An implant as recited in claim 48 wherein the press fit connection is a multiple zone press fit connection.

50. An implant as recited in claim 49 wherein the external surface of the base and the internal bore of the body are configured to mate to form a press fit connection.

51. An implant as recited in claim 50 wherein the press fit connection between the external surface and the internal bore of the body is a multiple zone press fit connection.

52. An implant as recited in claim 48 wherein the external surface of the base and the internal bore of the body are configured to mate to form a press fit connection.

53. An implant as recited in claim 52 wherein the press fit connection between the external surface and the internal bore of the body is a multiple zone press fit connection.

54. An implant as recited in claim 44 wherein the external surface of the base and the internal bore of the body are configured to mate to form a tapered fit connection.

55. An implant as recited in claim 54 wherein the internal channel of the base and the interference fit connector of the stem are configured to mate to form a tapered fit connection.

56. An implant as recited in claim 44 wherein the internal channel of the base and the interference fit connector of the stem are configured to mate to form a tapered fit connection.

57. An implant as recited in claim 56 wherein the external surface of the base and the internal bore of the body are configured to mate to form a tapered fit connection.

58. An implant as recited in claim 42 further comprising a securing element engaged with the top end of the stem, extending through the internal bore of the body, and connecting to the base, wherein the securing element secures the orientation of the base, body, and stem.

59. An implant as recited in claim 58 wherein the securing element is threaded into the stem.

60. An implant as recited in claim 42 wherein a securing element comprises a securing extension that protrudes from the top of the stem, through the internal bore of the body and through the base, and a securing fastener that is tightening onto the securing extension.

61. An implant as recited in claim 42 wherein the any of the interference fit connectors described are configured to function as expansion fit connectors.

62. An implant as recited in claim 42 wherein the any of the interference fit connectors described are configured to function as cam lock connectors.

63. A modular orthopedic implant comprising:
a tubular body with a top end, a opposing bottom end, a tissue engaging external portion between the top end and the bottom end, and an internal surface bounding an internal bore extending therebetween;
a base configured to provide an articulating portion on a first end and having an interference fit connector on a second end; and
a stem with a elongated shaft configured to be situated inside of a bone, and a top end having an interference fit connector, wherein the interference fit connector of the stem mates with the interference fit connector of the base to form a first press fit connection, and the interference fit connector of one of the stem and the base mates with the internal bore of the body to form a second press fit connection independently of formation of the first press fit connection.

64. An implant as recited in claim 63 wherein the first press fit connection is a multiple zone press fit connection.

65. An implant as recited in claim 63 wherein the second press fit connection is a multiple zone press fit connection.

66. An implant as recited in claim 63 wherein the first press fit connection is a multiple zone press fit connection and the second press fit connection is a multiple zone press fit connection.

* * * * *

UNITED STATES PATENT AND TRADEMARK OFFICE
CERTIFICATE OF CORRECTION

PATENT NO. : 6,887,276 B2  
APPLICATION NO. : 10/319139  
DATED : May 3, 2005  
INVENTOR(S) : Daniel E. Gerbec et al.

It is certified that error appears in the above-identified patent and that said Letters Patent is hereby corrected as shown below:

Column 1 Line 52 (background of the invention) Delete "issue" and ADD --tissue--

Column 2 Line 2 (background of the invention) Delete "patent's" and ADD --patient's--

Column 3 Line 50 (drawing descriptions) Delete "boy" ADD --body--

Column 6 Line 11 (detailed description) Delete "a" preceding "intervertebral disc" and ADD --an--

Column 9 Line 28 (detailed description) Delete "sodered" and ADD --soldered--

Column 11 Line 58 (detailed description) Delete "16" and ADD --10--

Column 15 Line 32 (claim 6) Delete "stern" and ADD --stem--

Column 16 Line 36 (claim 24) Delete "a" before "first external surface" and ADD --the--

Column 20 Line 9 (claim 60) Delete "tightening" and ADD --tightened--

Column 17 Line 23 (claim 36) Delete "Tighten" and ADD --tightening--

Column 18 Line 22 (claim 40) Delete "Tighten" and ADD --tightening--

Column 18 Line 43 (claim 41) Delete "Tighten" and ADD --tightening--

Column 15 Line 10 (claim 1) Delete "a" before "elongated" and ADD --an--

UNITED STATES PATENT AND TRADEMARK OFFICE
CERTIFICATE OF CORRECTION

| | |
|---|---|
| PATENT NO. | : 6,887,276 B2 |
| APPLICATION NO. | : 10/319139 |
| DATED | : May 3, 2005 |
| INVENTOR(S) | : Daniel E. Gerbec et al. |

It is certified that error appears in the above-identified patent and that said Letters Patent is hereby corrected as shown below:

Column 16 Line 20 (claim 22) Delete "a" before "elongated" and ADD --an--

Column 17 Line 10 (claim 35) Delete "a" before "elongated" and ADD --an--

Signed and Sealed this

Nineteenth Day of February, 2008

JON W. DUDAS
*Director of the United States Patent and Trademark Office*